US005808155A

United States Patent [19]
Shimada et al.

[11] Patent Number: 5,808,155

[45] Date of Patent: Sep. 15, 1998

[54] ELECTROPHOTOGRAPHIC PHOTOCONDUCTOR, CARBONATE COMPOUND FOR USE IN THE SAME, AND INTERMEDIATE COMPOUND FOR PRODUCING THE CARBONATE COMPOUND

[75] Inventors: Tomoyuki Shimada, Shizuoka-ken; Masaomi Sasaki, Susono; Chiaki Tanaka, Shizuoka-ken, all of Japan

[73] Assignee: Ricoh Company, Ltd., Tokyo, Japan

[21] Appl. No.: 812,696

[22] Filed: Mar. 6, 1997

Related U.S. Application Data

[62] Division of Ser. No. 422,930, Apr. 17, 1995, which is a division of Ser. No. 260,981, Jun. 15, 1994, Pat. No. 5,547,792.

[30] Foreign Application Priority Data

| | | | |
|---|---|---|---|
| Jun. 15, 1993 | [JP] | Japan | 5-168523 |
| Jun. 17, 1993 | [JP] | Japan | 5-171155 |
| Jun. 17, 1993 | [JP] | Japan | 5-171156 |
| Aug. 9, 1993 | [JP] | Japan | 5-217031 |
| Aug. 9, 1993 | [JP] | Japan | 5-217032 |
| Oct. 25, 1993 | [JP] | Japan | 5-288701 |

[51] Int. Cl.[6] ........................ C07C 211/03; C07C 211/21

[52] U.S. Cl. .......................... 564/355; 564/426; 564/427; 564/443

[58] Field of Search .................................... 564/355, 426, 564/427, 443

[56] References Cited

U.S. PATENT DOCUMENTS 5,604,065 2/1997 Shimada et al. .

OTHER PUBLICATIONS

CA:119:459741, Abstract of JP05027421, Ochiai, Feb. 5, 1993.

CA:106:121402, Abstract of JP61221155, Iwakura, Oct. 1, 1986.

CA:114:144430, Abstract of Macromolecules, Burkhart, vol. 24 No. 7 pp. 1511–1518, 1991.

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

An electrophotographic photoconductor having an electroconductive support and a photoconductive layer formed thereon containing as a photoconductive material at least one carbonate compound of formula (I):

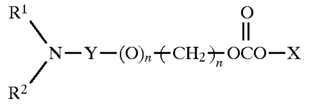

(I)

wherein $R^1$ and $R^2$ each is hydrogen, an alkyl group which may have a substituent, an aryl group which may have a substituent, or a condensed polycyclic group; Y is a bivalent arylene group which may have a substituent,

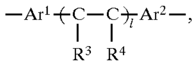

, or

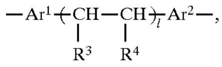

, in which $Ar^1$ and $Ar^2$ each is an arylene group which may have a substituent, $R^3$ and $R^4$ each is hydrogen, an alkyl group which may have a substituent or an aryl group which may have a substituent, and l is an integer of 1 or 2; and $R^1$ and $R^2$, or $R^1$ and Y may independently form a ring; X is an alkyl group which may have a substituent or an aryl group which may have a substituent; m is an integer or 0 or 1; and n is an integer of 0 to 6. In addition, a novel carbonate compound and a novel hydroxy compound as the intermediate material for the carbonate compound are disclosed.

8 Claims, 13 Drawing Sheets

ELECTROPHOTOGRAPHIC PHOTOCONDUCTOR, CARBONATE COMPOUND FOR USE IN THE SAME, AND INTERMEDIATE COMPOUND FOR PRODUCING THE CARBONATE COMPOUND

This is a division of application Ser. No. 08/422,930 filed on Apr. 17, 1995, now pending; which is a divisional application of Ser. No. 08/260,981 filed on Jun. 15, 1994, now U.S. Pat. No. 5,547,792.

BACKGROUND OF THE INVENTION

1. Field of the Invention

The present invention relates to an electrophotographic photoconductor comprising an electroconductive support and a photoconductive layer formed thereof. In addition, the present invention also relates to a carbonate compound which is effective as the organic photoconductive material for use in the photoconductor, and a hydroxy compound serving as the intermediate compound for producing the carbonate compound.

2. Discussion of Background

Conventionally, inorganic materials such as selenium, cadmium sulfide and zinc oxide are used as photoconductive materials of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed into a visible image by a developer comprising a coloring agent such as a dye or pigment, and a binder agent such as a polymeric material.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantaged, they have several shortcomings from the viewpoint of practical use.

For instance, a selenium photoconductor, which is widely used as present, satisfies the above-mentioned requirements (1) to (3) completely, but it has the shortcomings that the manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by dispersing cadmium sulfide particles and zinc oxide particles respectively in a binder resin, and coating the thus prepared coating liquid on a support. However, they are poor in mechanism properties, such as surface smoothness, hardness, tensile strength and wear resistance. Therefore, they cannot be used in the repeated operation, as they are.

To solve the problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as disclosed in Japanese Patent Publication 48-25648; a photoconductor comprising as the main component an organic pigment as disclosed in Japanese Laid-Open Patent Application 47-37543; a photoconductor comprising as the main component a eutectic crystal complex of a dye and a resin, as disclosed in Japanese Laid-Open Patent Application 47-10735; a photoconductor prepared by sensitizing a triphenylamine compound with a sensitizer pigment, as disclosed in U.S. Pat. No. 3,180,730; a photoconductor comprising an amine derivative as a charge transporting material, as disclosed in Japanese Laid-Open Patent Application 57-195254; a photoconductor comprising poly-N-vinylcarbazole and an amine derivative as charge transporting materials, as disclosed in Japanese Laid-Open Patent Application 58-1155; and a photoconductor comprising as a photoconductive material a polyfunctional tertiary amine compound, in particular, a benzidine compound, as disclosed in U.S. Pat. No. 3,265,496, Japanese Patent Publication 39-11546 and Japanese Laid-Open Patent Application 53-27033.

These electrophotographic photoconductors have their own excellent characteristics and considered to be valuable for practical use. With various requirements of the electrophotographic photoconductor in the electrophotographic process taken into consideration, however, the above-mentioned conventional electrophotographic photoconductors cannot always meet all the above-mentioned requirements.

Electrophotographic photoconductors which comprise carbonate-group-containing compounds as the photoconductive materials are disclosed in U.S. Pat. Nos. 4,801,517, 4,806,443 and 4,806,444, and Japanese Laid-Open Patent Applications Nos. 3-221522 and 4-11627. Each of the carbonate-group-containing compounds for use in the photoconductors is a polymeric compound, so that it is difficult to purify the carbonate-group-containing compound by column chromatography, recrystallization, distillation or sublimation in order to obtain such a high purity as required for the photoconductive material. Therefore, the impurities cannot completely be removed from the above-mentioned photoconductor, so that all the requirements for the photoconductor cannot be satisfied.

There is known an electrophotographic photoconductor of which photoconductive layer is prepared in such a manner that a low-molecular photoconductive material is dissolved or dispersed in a binder resin solution to form a resin composition and forming the photoconductive layer by casting the above prepared resin composition. However, when the photoconductive layer is formed using a mixture of the low-molecular photoconductive material and the binder resin, as previously mentioned, the resin solution of the photoconductive material easily tends to cause gelation to become white opaque, and induces phase separation depending on the kind of binder resin to be employed. As a result, the uniform photoconductive layer cannot be obtained, which has an adverse effect on the electrostatic properties and the durability of the photoconductor.

Furthermore, as described in Japanese Laid-Open Patent Application 3-221522, there are the problems of the gelation of a photoconductive layer coating liquid, and partial crystallization and cracks of the obtained photoconductive layer when a single high-molecular photoconductive material is used to prepare a coating liquid for the photoconductive layer. According to the description in the aforementioned application, it is necessary to control the copolymerization ratio of the high-molecular photoconductive material and adjust the viscosity of the coating liquid for the photoconductive layer to solve the above-mentioned problems.

Furthermore, a dihydroxy compound serving as a raw material for preparation of a charge transporting material is conventionally known, as disclosed in Japanese Laid-Open Patent Applications 1-105260 and 3-294251 and U.S. Pat. No. 4,801,517. A high-molecular charge transporting material is derived from the above-mentioned dihydroxy compound.

The following hydroxy compounds are conventionally known: o-(diphenylamino)phenol [Registry No. 25069-88-9], 3-(diphenylamino)phenol [Registry No. 107396-23-6], 4-(diphenylamino)phenol [Registry No. 25069-86-7], 3-{bis(4-methylphenyl)amino}phenol [Registry No. 80323-16-6], and 4-(diphenylamino)benzylalcohol [J. Polym. Sci. Polym. Chem. Ed., vol. 21, p. 969 (1983)].

SUMMARY OF THE INVENTION

It is therefore a first object of the present invention to provide an electrophotographic photoconductor comprising a photoconductive material, free from the conventional shortcomings, which can completely satisfy all the requirements in the electrophotographic process, including high durability, and can be easily be manufactured at relatively low cost.

A second object of the present invention is to provide a novel carbonate compound that can be employed as the photoconductive material in the electrophotographic photoconductor.

A third object of the present invention is to provide an intermediate compound for preparing the above-mentioned novel carbonate compound.

The above-mentioned first object of the present invention can be achieved by an electrophotographic photoconductor comprising an electroconductive support and a photoconductive layer formed thereon comprising as a photoconductive material at least one carbonate compound of formula (I):

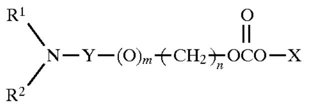

(I)

wherein $R^1$ and $R^2$ each is hydrogen, an alkyl group which may have a substituent, an aryl group which may have a substituent, or a condensed polycyclic group; Y is a bivalent arylene group which may have a substituent,

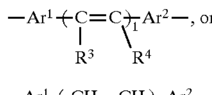

or

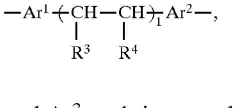

in which $Ar^1$ and $Ar^2$ each is an arylene group which may have a substituent, $R^3$ and $R^4$ each is hydrogen, an alkyl group which may have a substituent or an aryl group which may have a substituent, and l is an integer of 1 or 2; and $R^1$ and $R^2$, or $R^1$ and Y may independently form a ring; X is an alkyl group which may have a substituent or an aryl group which may have a substituent; m is an integer of 0 or 1; and n is an integer of 0 to 6.

The second object of the present invention can be achieved by a carbonate compound having formula (II):

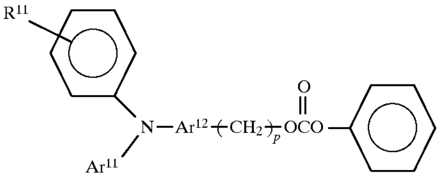

(II)

wherein $R^{11}$ is hydrogen, an alkyl group, an alkoxyl group, a phenyl group which may have a substituent, or a vinyl group which may have a substituent; $Ar^{11}$ is a phenyl group which may have a substituent, or a condensed polycyclic group; $Ar^{12}$ is a bivalent arylene group, a bivalent stilbene which may have a substituent, or a bivalent, 1,2-diphenylethane which may have a substituent; and p is an integer of 0 to 2.

The third object of the present invention can be achieved by a hydroxy compound of formula (III):

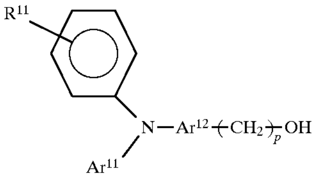

(III)

wherein $R^{11}$ is hydrogen, an alkyl group, an alkoxy group, a phenyl group which may have a substituent, or a vinyl group which may have a substituent; $Ar^{11}$ is a phenyl group which may have a substituent, or a condensed polycyclic group; $Ar^{12}$ is a bivalent arylene group, a bivalent stilbene which may have a substituent, or a bivalent 1,2-diphenylethane which may have a substituent; and p is an integer of 0 to 2.

Furthermore, a hydroxy compound of formula (III') can also attain the same object as mentioned above:

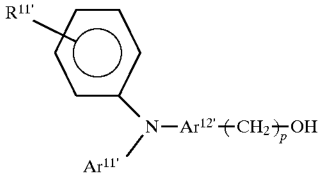

(III')

wherein $R^{11'}$ is hydrogen, an alkyl group, an alkoxyl group, a phenyl group which may be substituted by an alkyl group, or a diphenylamino group which may be substituted by an alkyl group; $Ar^{11'}$ is a phenyl group which may be substituted by an alkyl group, a biphenylyl group which may be substituted by an alkyl group, or a condensed polycyclic group; $Ar^{12'}$ is a phenylene group, a biphenylene group, or a bivalent stilbene group; and p is an integer of 0 to 2, provided that such conditions that $R^{11'}$ is hydrogen or an alkyl group, $Ar^{11'}$ is phenyl group which may have an alkyl group as a substituent, $Ar^{12'}$ is a phenylene group and p is 0 or 1 are not satisfied at the same time.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
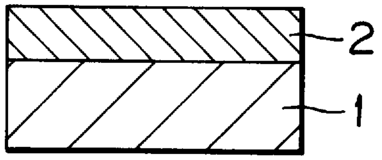
FIG. 1 is a schematic cross-sectional view of a first example of an electrophotographic photoconductor according to the present invention.

An electrophotographic photoconductor according to the present invention comprises an electroconductive support and a photoconductive layer formed thereon comprising as the photoconductive material at least one carbonate compounds of formula (I):

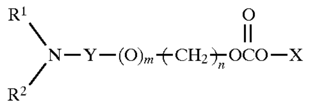

(I)

wherein $R^1$ and $R^2$ each is hydrogen, an alkyl group which may have a substituent, an aryl group which may have a substituent, or a condensed polycyclic group; Y is a bivalent arylene group which may have a substituent,

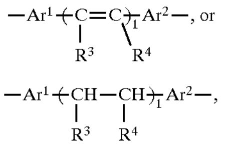

in which $Ar^1$ and $Ar^2$ each is an arylene group which may have a substituent, $R^3$ and $R^4$ each is hydrogen, an alkyl group which may have a substituent or an aryl group which may have a substituent, and l is an integer of 1 or 2; and $R^1$ and $R^2$, or $R^1$ and Y may independently form a ring; X is an alkyl group which may have a substituent or an aryl group which may have a substituent; m is an integer of 0 or 1; and n is an integer of 0 to 6.

Specific examples of $R^1$, $R^2$, Y and X, and the substituent for $R^1$, $R^2$, Y and X in formula (I) are as follows:

(1) Halogen atom such as fluorine, chlorine, bromine and iodine.

(2) Cyano group.

(3) Nitro group.

(4) Methylenedioxy group;

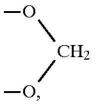

and methylenedithio group:

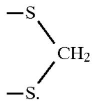

(5) Alkyl group represent by ($—R^5$), in particular a straight-chain or branched-chain alkyl group having 1 to 12 carbon atoms, more preferably 1 to 9 carbon atoms, further preferably 1 to 4 carbon atoms. The above alkyl group may have a substituent such as a fluorine atom, a hydroxyl group, a cyano group, an alkoxyl group having 1 to 4 carbon atoms, a phenyl group which may have a substituent such as an alkyl group having 1 to 4 carbon atoms or an alkoxyl group having 1 to 4 carbon atoms, and a halogen.

Specific examples of the above alkyl group include methyl group, ethyl group, n-propyl group, i-propyl group, tert-butyl group, sec-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(6) Alkoxyl group represented by $—OR^5$, in which $R^5$ represents the same alkyl group as defined in (5).

Specific examples of the above alkoxyl group include methoxy group, ethoxy group, n-propoxy group, i-propoxy group, tert-butoxy group, n-butoxy group, sec-butoxy group, i-butoxy group, 2-hydroxyethoxy group, 2-cyanoethoxy group, benzyloxy group, 4-methylbenzyloxy group and trifluoromethoxy group.

(7) Aryl groups represented by $—Ar^3$, such as a carbocyclic aromatic group and a heterocyclic aromatic group.

Specific examples of the above carbocyclic aromatic group include phenyl group, biphenyl group, terphenyl group, a monovalent group of cyclophane, pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Specific examples of the above heterocyclic aromatic group include pyridyl group, pyrimidyl group, pyrazinyl group, triazinyl group, furyl group, pyrrolyl group, thienyl group, quinolyl group, coumarinyl group, benzofuranyl group, benzindazolyl group, benzoxazolyl group, dibenzofuranyl group, benzothienyl group, dibenzothienyl group, indolyl group, carbazolyl group, pyrazolyl group, imidazolyl group, oxazolyl group, isooxazolyl group, thiazolyl group, indazolyl group, benzothiazolyl group, pyridazinyl group, cinnolinyl group, quinazolinyl group, quinoxalyl group, phthalazinyl group, phthalazinedionyl group, chromonyl group, naphtholactonyl group, quinolonyl group, o-sulfobenzoic acid imidyl group, maleic acid imidyl group, naphthalidinyl group, benzimidazolonyl group, benzoxazolonyl group, benzthiazolonyl group, benzthiazothionyl group, quinazolonyl group, quinoxalonyl group, phthalazonyl group, dioxopyrimidinyl group, pyridonyl group, isoquinolonyl group, isoquinolyl group, isothiazolyl group, benzisooxazolyl group, benzisothiazolyl group, indazolonyl group, acridinyl group, acridonyl group, quinazolinedionyl group, quinoxalinedionyl group, benzoxazinedionyl group, benzoxazinyl group, naphthalimidyl group, tetrahydrofuryl group, tetrahydrothienyl group, piperadino group, piperadinyl group and pyrrolidinyl group.

(8) Aryloxy group represented by —$OAr^3$, in which $Ar^3$ represents the same aryl group as defined in (7).

Specific examples of the above aryloxy group include phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(9) Alkylthio group represented by —$SR^5$, in which $R^5$ represents the same alkyl group as defined in (2).

Specific examples of the above alkylthio group include methylthio group, ethylthio group and benzylthio group.

(10) Arylthio group represented by —$SAr^3$, in which $Ar^3$ represents the same aryl group as defined in (7).

Specific examples of the above arylthio group include phenylthio group, tolylthio group and naphthylthio group.

(11) Amino group of:

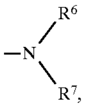

in which $R^6$ and $R^7$ each is hydrogen, the same alkyl group as defined in (5), or the same aryl group as defined in (7), and $R^6$ and $R^7$ may form a ring in combination.

Specific examples of the above amino group represented by:

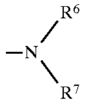

include amino group, dimethylamino group, diphenylamino group, ditolylamino group, piperidino group, morpholino group, julolidino group and carbazolyl group.

(12) Arylene group represented by —$Ar^4$—, such as the same bivalent carbocyclic aromatic group and heterocyclic aromatic group as previously described in (7).

Specific examples of the arylene group include phenylene group, biphenylene group, naphthylene group, methylphenylene group, 9,9-dimethyl-2,7-fluorenylene group and thiophene-2,5-di-yl group.

Specific examples of the carbonate compound of formula (I) used as the photoconductive material in the present invention are shown in the following Table 1:

TABLE 1
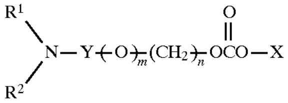
| Compound No. | $R^1$ | $R^2$ | Y | m | n | X |
| --- | --- | --- | --- | --- | --- | --- |
| 1 | H | H | 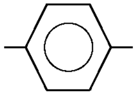 | 0 | 0 | 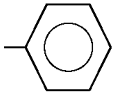 |
| 2 | $-CH_3$ | $-CH_3$ | " | " | " | " |
| 3 | 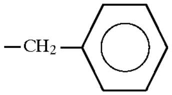 | 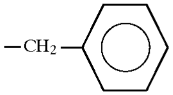 | " | " | " | " |
| 4 | 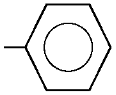 | 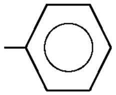 | " | " | " | " |
| 5 | 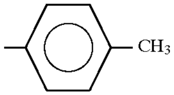 | 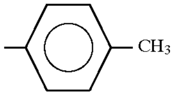 | " | " | " | " |
| 6 | 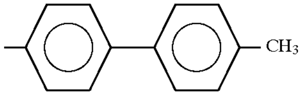 | 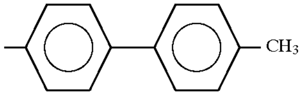 | " | " | " | " |
| 7 | 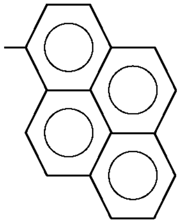 | 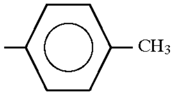 | " | " | " | " |

TABLE 1-continued
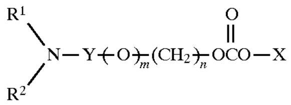
| Compound No. | $R^1$ | $R^2$ | Y | m | n | X |
| --- | --- | --- | --- | --- | --- | --- |
| 8 | 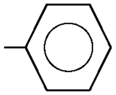 | 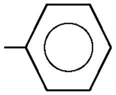 | 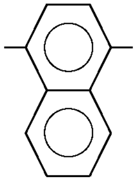 | " | " | " |
| 9 | 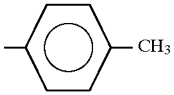 | 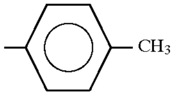 | 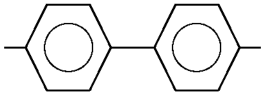 | " | " | " |
| 10 | 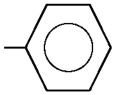 | 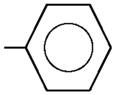 | 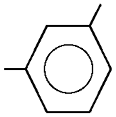 | " | " | " |
| 11 | 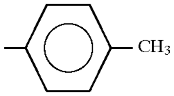 | 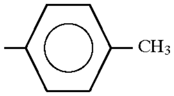 | 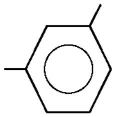 | " | " | " |
| 12 | 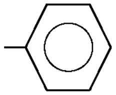 | 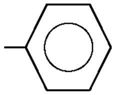 | 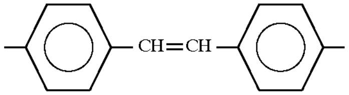 | 0 | 0 | 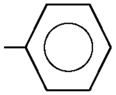 |
| 13 | 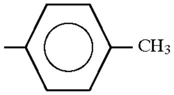 | 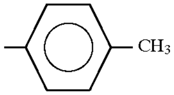 | " | " | " | " |

TABLE 1-continued
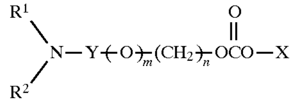
| Compound No. | $R^1$ | $R^2$ | Y | m | n | X |
|---|---|---|---|---|---|---|
| 14 | 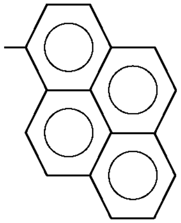 | " | 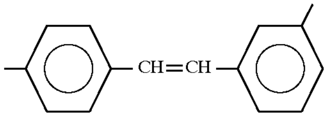 | " | " | " |
| 15 | 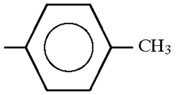 | " | " | " | " | " |
| 16 | 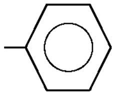 | 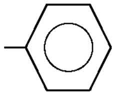 | 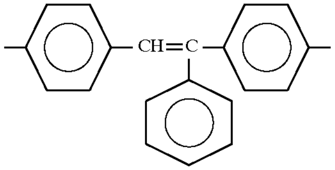 | " | " | " |
| 17 | 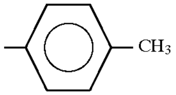 | 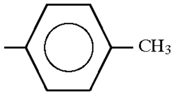 | " | " | " | " |
| 18 | 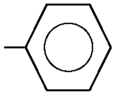 | " | 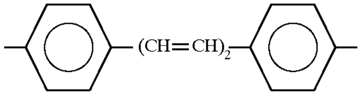 | " | " | " |
| 19 | " | 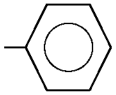 | 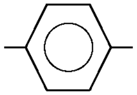 | " | 2 | " |

TABLE 1-continued
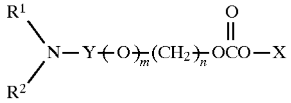
| Compound No. | $R^1$ | $R^2$ | Y | m | n | X |
| --- | --- | --- | --- | --- | --- | --- |
| 20 | 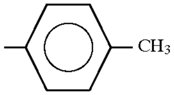 | 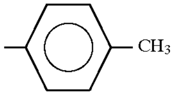 | " | " | 2 | " |
| 21 | 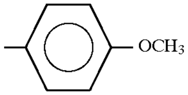 | 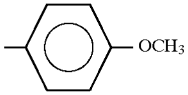 | " | " | 2 | " |
| 22 | 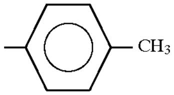 | 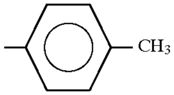 | 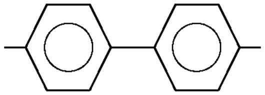 | " | 2 | " |
| 23 | 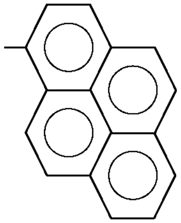 | 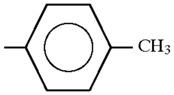 | 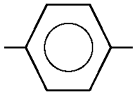 | 0 | 2 | 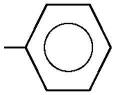 |
| 24 | " | 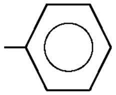 | 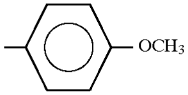 | " | " | " |
| 25 | " | 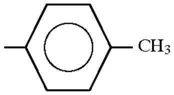 | " | " | " | " |

TABLE 1-continued
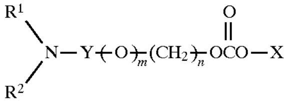
| Compound No. | $R^1$ | $R^2$ | Y | m | n | X |
|---|---|---|---|---|---|---|
| 26 | " | 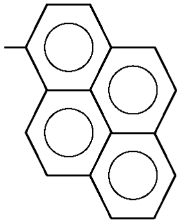 | " | " | " | " |
| 27 | 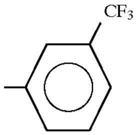 | 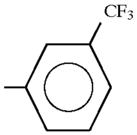 | 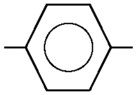 | " | 0 | " |
| 28 | 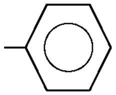 | 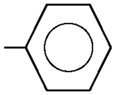 | " | " | " | 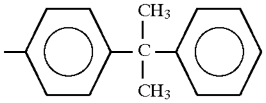 |
| 29 | 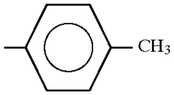 | 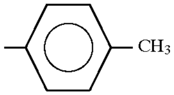 | " | " | 2 | " |
| 30 | 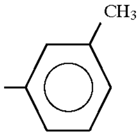 | 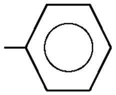 | " | " | 0 | $-CH_2CH_2CH_2CH_3$ |
| 31 | 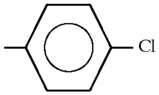 | 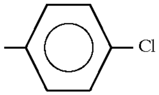 | 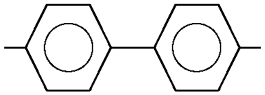 | " | " | $-CH_2CH_2OCH_2CH_3$ |

TABLE 1-continued
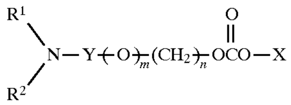
| Compound No. | $R^1$ | $R^2$ | Y | m | n | X |
|---|---|---|---|---|---|---|
| 32 | 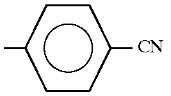 | 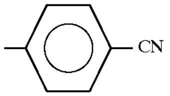 | 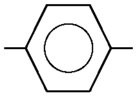 | 1 | 2 | 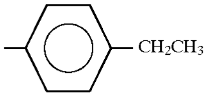 |
| 33 | 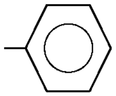 | 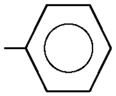 | 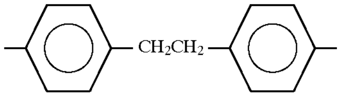 | 0 | 0 | 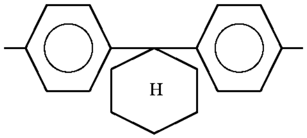 |
| 34 | 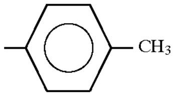 | 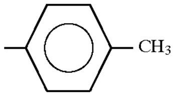 | 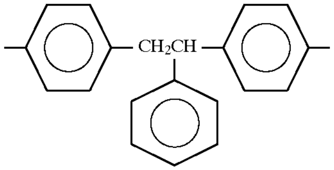 | 0 | 0 | 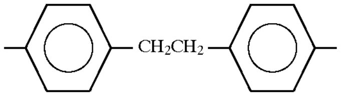 |
| 35 | 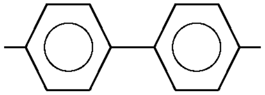 | 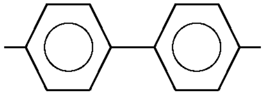 | 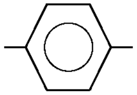 | 1 | 6 | 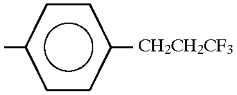 |
| 36 | 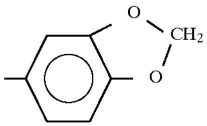 | 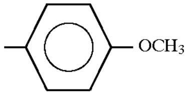 | 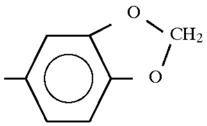 | 0 | 1 | 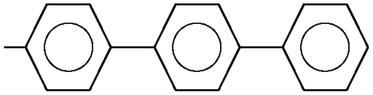 |

TABLE 1-continued
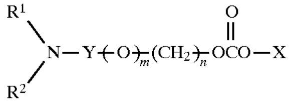
| Compound No. | $R^1$ | $R^2$ | Y | m | n | X |
|---|---|---|---|---|---|---|
| 37 | 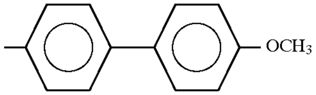 | 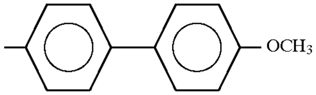 | 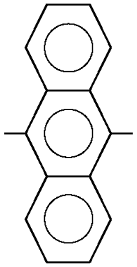 | " | " | 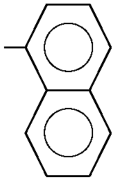 |
| 38 | 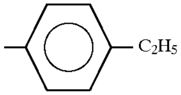 | 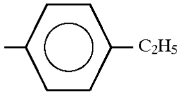 | 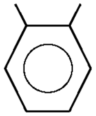 | " | 4 | 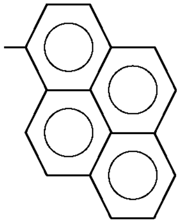 |
| 39 | 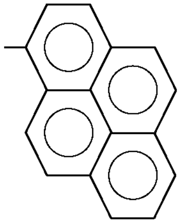 | 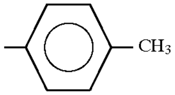 | 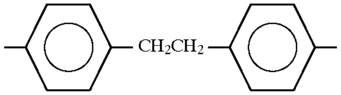 | " | 0 | 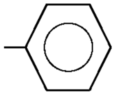 |

TABLE 1-continued
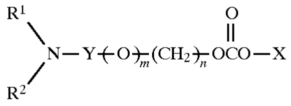
| Compound No. | $R^1$ | $R^2$ | Y | m | n | X |
|---|---|---|---|---|---|---|
| 40 | 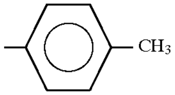 | 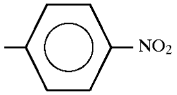 | 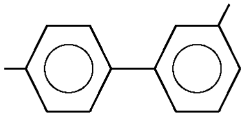 | " | 2 | 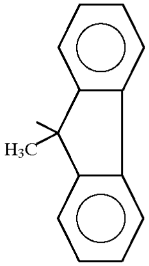 |
| 41 | | 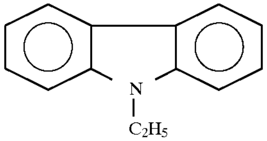 | | " | 0 | 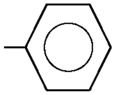 |
| 42 | | 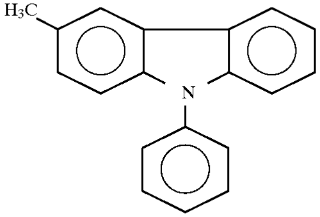 | | " | 2 | " |
| 43 | | 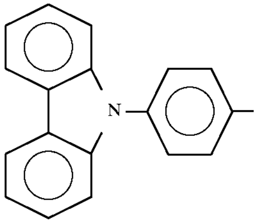 | | " | " | " |

TABLE 1-continued
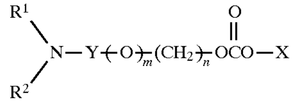
| Compound No. | $R^1$ | $R^2$ | Y | m | n | X |
|---|---|---|---|---|---|---|
| 44 | 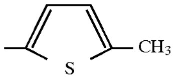 | 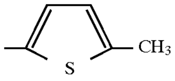 | 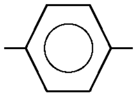 | 0 | 0 | 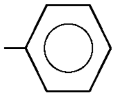 |
| 45 | 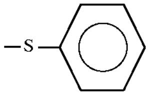 | 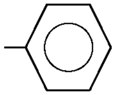 | 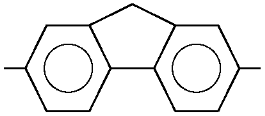 | " | " | " |
| 46 | 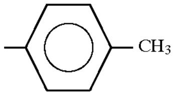 | 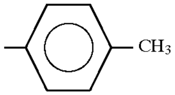 | 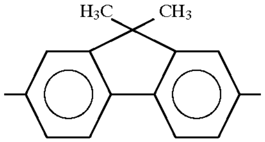 | " | " | " |
| 47 | 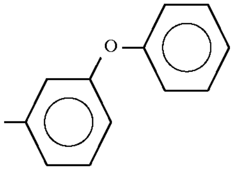 | 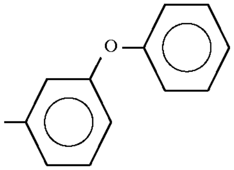 | 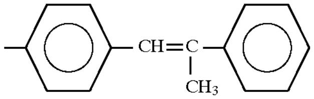 | " | 2 | 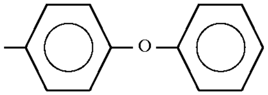 |
| 48 | 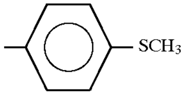 | 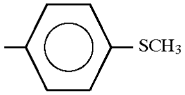 | 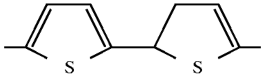 | " | 0 | 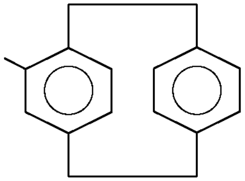 |
| 49 | 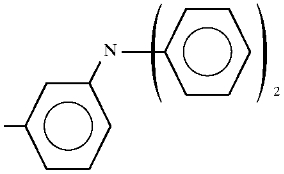 | 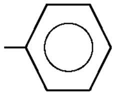 | 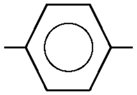 | " | 2 | 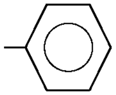 |

TABLE 1-continued
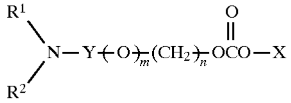
| Compound No. | $R^1$ | $R^2$ | Y | m | n | X |
|---|---|---|---|---|---|---|
| 50 | 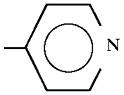 | 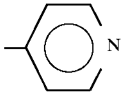 | 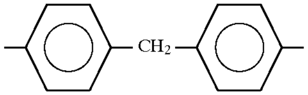 | " | 3 | 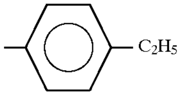 |
| 51 | 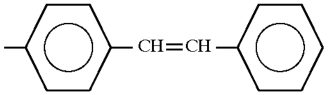 | 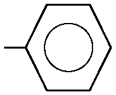 | 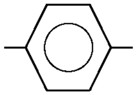 | " | 0 | 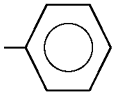 |
| 52 | 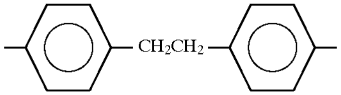 | 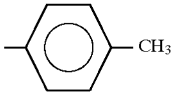 | " | " | 2 | " |
| 53 | 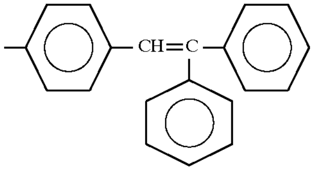 | 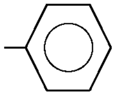 | " | " | 0 | " |

The carbonate compound of formula (I) for use in the photoconductor of the present invention can be obtained, for example, by allowing a hydroxy compound of formula (IV) to react with a chloroformate compound of formula (V):

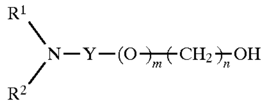

(IV)

wherein $R^1$, $R^2$, Y, m and n are the same as previously defined in formula (I):

(V)

wherein X is the same as previously defined in formula (I).

Furthermore, in the present invention, a novel carbonate compound of formula (II) can also be employed as the photoconductive material in the photoconductor of the present invention:

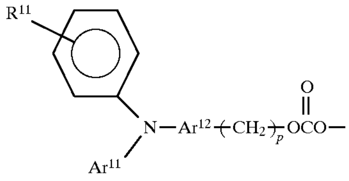

(II)

wherein $R^{11}$ is hydrogen, an alkyl group, an alkoxyl group, a phenyl group which may have a substituent, or a vinyl group which may have a substituent; $Ar^{11}$ is a phenyl group which may have a substituent, or a condensed polycyclic group; $Ar^{12}$ is a bivalent arylene group, a bivalent stilbene which may have a substituent, or a bivalent 1,2-diphenylethane which may have a substituent; and p is an integer of 0 to 2.

Specific examples of the alkyl group of $R^{11}$ in formula (II) are methyl group, ethyl group, propyl group and butyl group.

Specific examples of the alkoxy group of $R^{11}$ in formula (II) are methoxy group, ethoxy group, propoxy group and butoxy group.

Specific examples of the arylene group of $Ar^{12}$ in formula (II) are phenylene group and biphenylene group.

Specific examples of the condensed polycyclic group of $Ar^{11}$ in formula (II) are naphthyl group, anthryl group, and pyrenyl group.

Specific examples of the substituted vinyl group of $R^{11}$ in formula (II) are styryl group, β-phenylstyryl group, and β-methylstyryl group.

Specific examples of the substituted phenyl group of $R^{11}$ and $Ar^{11}$ in formula (II) are methylphenyl group, methoxyphenyl group, biphenylyl group, methylbiphenyl group and methoxybiphenyl group.

Specific examples of the substituted bivalent stilbene group of $Ar^{12}$ in formula (II) are bivalent α-phenylstilbene and bivalent α-methylstilbene.

As the substituted bivalent 1,2-diphenyl ethane of $Ar^{12}$ in formula (II), 1,1,2-triphenylethane can be employed.

Such a novel carbonate compound of formula (II) can be obtained, for example, by allowing a hydroxy compound of formula (III) to react with phenyl chloroformate of formula (V)-1 in the presence of a catalyst in a solvent, or without any solvent:

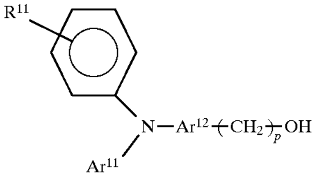

(III)

wherein $R^{11}$, $Ar^{11}$, $Ar^{12}$ and p are the same as previously defined in formula (II).

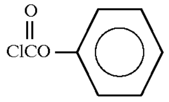

(V)-1

In this case, nitrogen-containing compounds such as diethylamine, triethylamine, tripropylamine, pyridine and quinoline; and hydroxides of alkaline metals such as sodium hydroxide and potassium hydroxide can be used as the catalyst in the above reaction. The catalyst may be added to the reaction mixture in a sufficient amount for neutralizing hydrogen chloride generated in the course of the reaction. More specifically, the amount of the catalyst is preferably from an equivalent amount of the reactive group, to three times the equivalent amount of the reactive group.

In this case, dichloromethane, chloroform, carbon tetrachloride, tetrahydrofuran, ethyl ether, toluene, xylene, acetone, methyl ethyl ketone, cyclohexane, and hexane can be used as the solvents.

The reaction is carried out at 0° to 150° C., more preferably at 5° to 50° C.

The hydroxy compound of the following formula (III), serving as the intermediate compound for producing the carbonate compound of formula (II), is a novel compound;

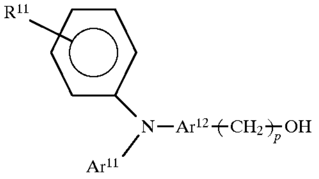

(III)

wherein $R^{11}$, $Ar^{11}$, $Ar^{12}$ and p are the same as previously defined in formula (II).

In the case where p=0 in the formula (III) of the hydroxy compound, the hydroxy compound can be obtained by cleavage of an arylalkyl ether compound of formula (VI):

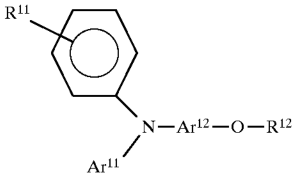

(VI)

wherein $R^{11}$, $Ar^{11}$, and $Ar^{12}$ are the same as previously defined in formula (III); and $R^{12}$ is an alkyl group.

More specifically, the cleavage of an arylalkyl ether compound of formula (VI) can be carried out using an acid reagent or a basic reagent. Examples of the acid reagent are hydrogen bromide, hydrogen iodide, trifluoroacetic acid, pyridine hydrochloride, concentrated hydrochloric acid, magnesium iodide etherate, aluminum chloride, aluminum bromide, boron tribromide, boron trichloride, and boron triiodide. Examples of the basic reagent are potassium hydroxide, lithium diphenylphosphide, and sodium thiolate.

In the cleavage reaction, acetic anhydride, dichloromethane, tetrahydrofuran (THF), dimethylformamide (DMF), pyridine and butanol can be employed as the solvent. The reaction temperature, which varies depending on the reactivity of the reagent to be employed in the reaction, is generally in the range from a room temperature to 200° C.

In the case where p=1 in the formula (III) of the hydroxy compound, the hydroxy compound can be obtained by the reduction of an aldehyde compound of formula (VII):

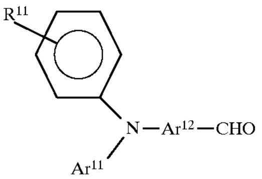

(VII)

wherein $R^{11}$, $Ar^{11}$, and $Ar^{12}$ are the same as previously defined in formula (III).

In this case, the reduction reaction is carried out at 0° C. to a room temperature in a solvent such as ethyl ether, methanol, or tetrahydrofuran, using a reducing reagent, for instance, lithium aluminum hydride or sodium boron hydride.

In the case where p=2 in the formula (III) of the hydroxy compound, the hydroxy compound can be obtained by adding butyl lithium to a halide of formula (VIII) to prepare a lithium salt, and hydrolyzing the lithium salt with the addition of ethylene oxide:

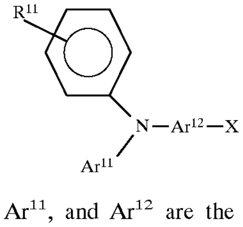

(VIII)

wherein $R^{11}$, $Ar^{11}$, and $Ar^{12}$ are the same as previously defined in formula (III); and X is a halogen atom.

In this case, dichloromethane, toluene or hexane can be employed as the solvent. After the lithium salt is prepared at a room temperature to 100° C., the reaction system is cooled to about −40° C. With the addition of ethylene oxide to the lithium salt, the temperature of the reaction system is gradually increased to room temperature, and the hydrolyzing is carried out.

As the specific example of the hydroxy compound of formula (III), a hydroxy compound of the following formula (III') can be employed:

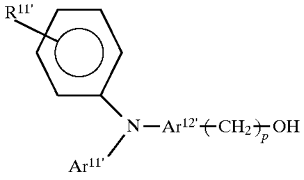

(III')

wherein $R^{11'}$ is hydrogen, an alkyl group, an alkoxyl group, a phenyl group which may be substituted by an alkyl group, or a diphenylamino group which may be substituted by an alkyl group; $Ar^{11'}$ is a phenyl group which may be substituted by an alkyl group, a biphenylyl group which may be substituted by an alkyl group, or a condensed polycyclic group; $Ar^{12'}$ is a phenylene group, a biphenylene group, or a bivalent stilbene group; and p is an integer of 0 to 2, provided that such conditions that $R^{11'}$ is hydrogen or an alkyl group, $Ar^{11'}$ is phenyl group which may have an alkyl group as a substituent, $Ar^{12'}$ is a phenylene group and p is 0 or 1 are not satisfied at the same time.

For example, when N,N-bis(4-methylphenyl)-4-amino-3'-hydroxystilbene of formula (III)-1 is allowed to react with bis(chloroformate) of formula (V)-2, a carbonate compound (II') serving as a charge transporting material can be obtained:

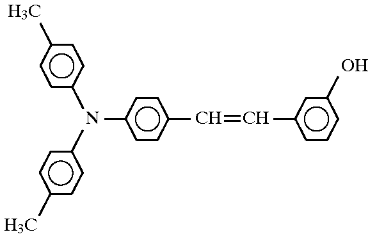

(III)-1

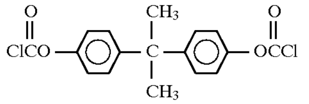

(V)-2

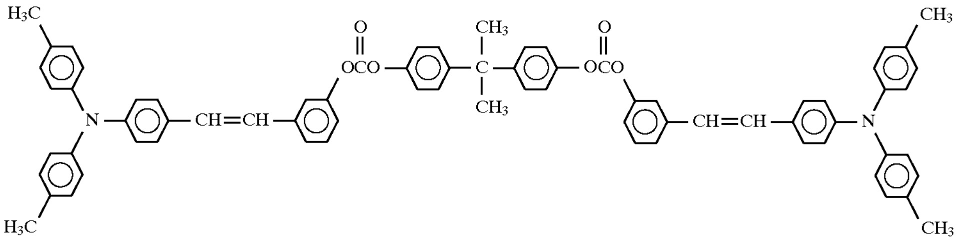

(II')

The carbonate compound of formula (I), and a novel carbonate compound of formula (II) according to the present invention, which are remarkably effective as the photoconductive materials in the electrophotographic photoconductor, are optically or chemically sensitized with a sensitizer such as a dye or Lewis acid. In addition, the carbonate compounds of formulas (I) and (II) effectively function as charge transporting materials in a function-separating electrophotographic photoconductor where an organic or inorganic pigment serves as a charge generating material.

In the photoconductors according to the present invention, at least one carbonate compound of the formula (I) or (II) is contained in the photoconductive layers 2, 2*a*, 2*b*, 2*c* and 2*d*. The carbonate compounds can be employed in different ways, for example, as shown in FIGS. 1 through 5.

In the photoconductor as shown in FIG. 1, a photoconductive layer 2 is formed on an electroconductive support 1, which photoconductive layer 2 comprises at least one carbonate compound of formula (I) or (II), a sensitizing dye and a binder agent (binder resin). In this photoconductor, the carbonate compound works as a photoconductive material, through which charge carriers which are necessary for the light decay of the photoconductor are generated and transported. However, the carbonate compound itself scarcely absorbs light in the visible light range and, therefore, it is necessary to add a sensitizing dye which absorbs light in the visible light range in order to form latent electrostatic images by use of visible light.

Figure 2:
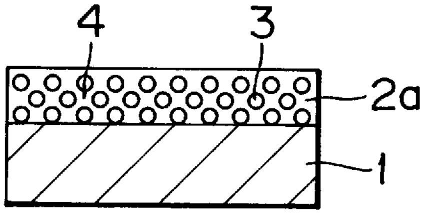
FIG. 2 is a schematic cross-sectional view of a second example of an electrophotographic photoconductor according to the present invention.

Referring to FIG. 2, there is shown an enlarged cross-sectional view of another embodiment of an electrophotographic photoconductor according to the present invention. In the figure, reference number 1 indicates an electroconductive support. On the electroconductive support 1, where is formed a photoconductive layer 2*a* comprising a charge generating material 3 dispersed in a charge transporting medium 4 comprising at least one carbonate compound of formula (I) or (II) and a binder agent. In this embodiment, the carbonate compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the carbonate compound not overlap in the visible light range. This is because, in order that the charge generating material 3 produce charge carriers efficiently, it is necessary that light pass through the charge transporting medium 4 and reach the surface of the charge generating material 3. Since the carbonate compound of formula (I) or (II) does not substantially absorb light in the visible range, it can work effectively as a charge transporting material in combination with the charge generating material 3 which absorbs the light in the visible region and generates charge carriers.

Figure 3:
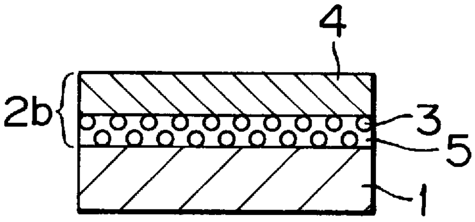
FIG. 3 is a schematic cross-sectional view of a third example of an electrophotographic photoconductor according to the present invention.

Referring to FIG. 3, there is shown an enlarged cross-sectional view of a further embodiment of an electrophotographic photoconductor according to the present invention. In the figure, there is formed on an electroconductive support 1 a two-layered photoconductive layer 2*b* comprising a charge generation layer 5 containing the charge generating material 3, and a charge transport layer 4 containing at least one carbonate compound of the previously described formula (I) or (II).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, and the charge carriers are accepted and transported by the charge transport layer 4. In the charge transport layer 4, the carbonate compound mainly works for transporting charge carriers. The generation and transportation of the charge carriers are performed by the same mechanism as that in the photoconductor shown in FIG. 2.

Figure 4:
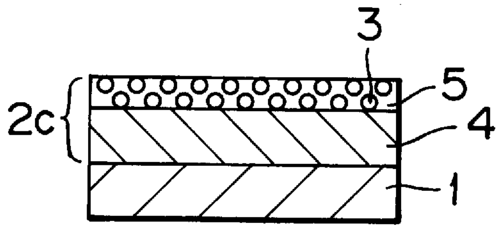
FIG. 4 is a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of the charge generation layer 5 and the charge transport layer 4 is reversed in view of the electrophotographic photoconductor as shown in FIG. 3. The mechanism of the generation and transportation of charge carriers is substantially the same as that of the photoconductor shown in FIG. 3.

Figure 5:
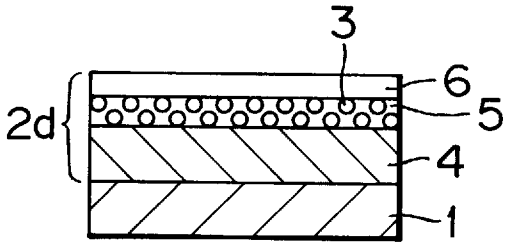
FIG. 5 is a schematic cross-sectional view of a fifth example of an electrophotographic photoconductor according to the present invention.

In the above photoconductor, with the mechanical strength taken into consideration, a protective layer 6 may be formed on the charge generation layer 5 as shown in FIG. 5.

When the electrophotographic photoconductor according to the present invention as shown in FIG. 1 is prepared, at least one carbonate compound of the previously described formula (I) or (II) is dissolved in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 $\mu$m, more preferably in the range of 5 to 20 $\mu$m. It is preferable that the amount of the carbonate compound contained in the photoconductive layer 2 be in the range or 30 to 70 wt. %, more preferably about 50 wt. %, of the total weight of the photoconductive layer 2.

It is preferable that the amount of the sensitizing dye contained in the photoconductive layer 2 be in the range of 0.1 to 5 wt. %, more preferably in the range of 0.5 to 3 wt. %, of the total weight of the photoconductive layer 2.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl) thiapyrylium perchlorate and a benzopyrylium salt (described in Japanese Patent Publication 48-25658). These sensitizing dyes can be used alone or in combination.

The electrophotographic photoconductor shown in FIG. 2 can be obtained by dispersing finely-divided particles of the charge generating material 3 in a solution in which at least one carbonate compound of formula (I) or (II) and the binder agent are dissolved, coating the above-prepared dispersion on the electroconductive support 1 and then drying the same to form the photoconductive layer 2*a*.

It is preferable that the thickness of the photoconductive layer 2*a* be in the range of 3 to 50 $\mu$m, more preferably in the range of 5 to 20 $\mu$m. It is preferable that the amount of the carbonate compound contained in the photoconductive layer 2*a* be in the range or 10 to 95 wt. %, more preferably in the range of 30 to 90 wt. %, of the total weight of the photoconductive layer 2*a*.

It is preferable that the amount of the charge generating material 3 contained in the photoconductive layer 2*a* be in the range of 0.1 to 50 wt. %, more preferably in the range of 1 to 20 wt. %, of the total weight of the photoconductive layer 2*a*.

Specific examples of the charge generating material 3 for use in the present invention are as follows: inorganic pigments such as selenium, selenium - tellurium, cadmium sulfide, cadmium sulfide - selenium and $\alpha$-silicon (amorphous silicon); and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and parylene pigments such as Algol Scarlet B and Indanthrene Scarlet R (made by Bayer Co., Ltd.). These charge generating materials may be used alone or in combination.

The electrophotographic photoconductor shown in FIG. 3 can be obtained by the following method:

The charge generating material 3 is vacuum-deposited on the electroconductive support 1 to form the charge generation layer 5 on the support 1. Alternatively, finely-divided particles of the charge generating material 3 are dispersed in an appropriate solvent, in which the binder agent may be dissolved when necessary, to prepare a dispersion, and the thus prepared dispersion is coated on the electroconductive support 1 and dried, so that the charge generation layer 5 is formed. When necessary, the charge generation layer 5 is subjected to surface treatment by buffing and adjustment of the thickness thereof. On the thus formed charge generation layer 5, a coating solution in which at least one carbonate compound of formula (I) or (II) and the binder agent are dissolved is coated and dried, so that the charge transport layer 4 is formed. The same charge generating materials as employed in the above-mentioned photoconductive layer 2*a* can be used in the charge generation layer 5.

In this case, the thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is formed by coating the dispersion of the finely-divided particles of the charge generating material 3, it is preferable that the amount of finely-divided particles of the charge generating material 3 contained in the charge generation layer 5 be in the range of 10 to 95 wt. %, more preferably in the range of about 50 to 90 wt. %, or the total weight of the charge generation layer 5. It is preferable that the amount of the carbonate compound contained in the charge transport layer 4 be in the range of 10 to 95 wt. %, more preferably in the range of 30 to 90 wt. %, of the total weight of the charge transport layer 4.

The electrophotographic photoconductor shown in FIG. 4 can be obtained by the following method:

A coating solution in which the carbonate compound and the binder agent are dissolved is coated on the electroconductive support 1 and dried to form the charge transport layer 4. On the thus formed charge transport layer 4, a dispersion prepared by dispersing finely-divided particles of the charge generating material 3 in a solvent, in which the binder agent may be dissolved when necessary, is coated by spray coating and dried to form the charge generation layer 5 on the charge transport layer 4. The amount ratio of the components contained in the charge generation layer and charge transport layer is the same as previously described in FIG. 3.

The electrophotographic photoconductor shown in FIG. 5 can be obtained by forming a protective layer 6 on the charge generation layer 5 as obtained in FIG. 4 by spray-coating of an appropriate resin solution. As a resin for use in the protective layer 6, any of binder agents to be described later can be used.

Specific examples of the material for the electroconductive support 1 include a metallic plate or foil made of aluminum, a plastic film on which a metal such as aluminum is deposited, and a sheet of paper which has been treated so as to be electroconductive.

Specific examples of the binder agent used in the preparation of the photoconductor are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed.

Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductor according to the present invention, an adhesive layer or a barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductor according to the present invention, the surface of the photoconductor is uniformly charged to a predetermined polarity in the dark. The uniformly charged photoconductor is exposed to a light image so that a latent electrostatic image is formed on the surface of the photoconductor. The thus formed latent electrostatic image is developed to a visible image by a developer, and the developed image can be transferred to a sheet of paper when necessary. The photosensitivity and the flexibility of the electrophotographic photoconductor according to the present invention are remarkably improved.

Other features of this invention will become apparent in the course of the following description of exemplary embodiments, which are given for illustration of the invention and are not intended to be limiting thereof.

Preparation Example 1-1

[Synthesis of N,N-bis(4-methylphenyl)-4-amino-3'-hydroxystilbene]

40 ml of N,N-dimethylformamide were added to a mixture of 4.06 g (10.0 mmol) of N,N-bis(4-methylphenyl)-4-amino-3'-methoxystilbene and 1.68 g (20.0 mmol) of sodium thioethylate. The thus prepared mixture was refluxed with stirring for 4 hours. The mixture was then cooled to room temperature, and poured into water. The ether component was extracted from the reaction mixture by a separating funnel. The thus obtained organic layer was washed with water, and dried over magnesium sulfate and further dried under reduced pressure, thereby producing a dark green oily material.

The thus obtained material was chromatographed on a silica gel column using toluene as an eluting solution, and the product thus obtained was recrystallized from a mixed solvent of toluene and n-hexane, so that N,N-bis(4-methylphenyl)-4-amino-3'-hydroxystilbene of formula (III)-1 precipitated as yellow crystals in the form of needles. The yield was 3.26 g (83.4%).

(III)-1

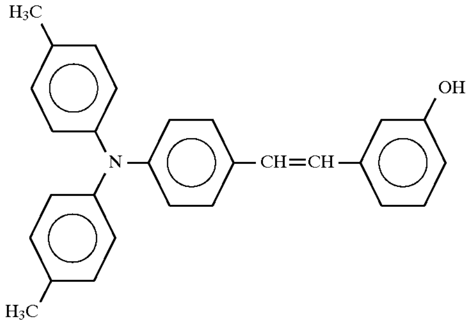

The melting point of the above hydroxy compound was 157.0° and 158.0° C.

The results of the elemental analysis of the thus obtained compound were as follows:

| | % C | % H | % N |
|---|---|---|---|
| Calculated | 85.90 | 6.44 | 3.58 |
| Found | 86.34 | 6.52 | 3.58 |

The above calculation was based on the formula for N,N-bis(4-methylphenyl)-4-amino-3'-hydroxystilbene of $C_{28}H_{25}NO$.

Figure 8:
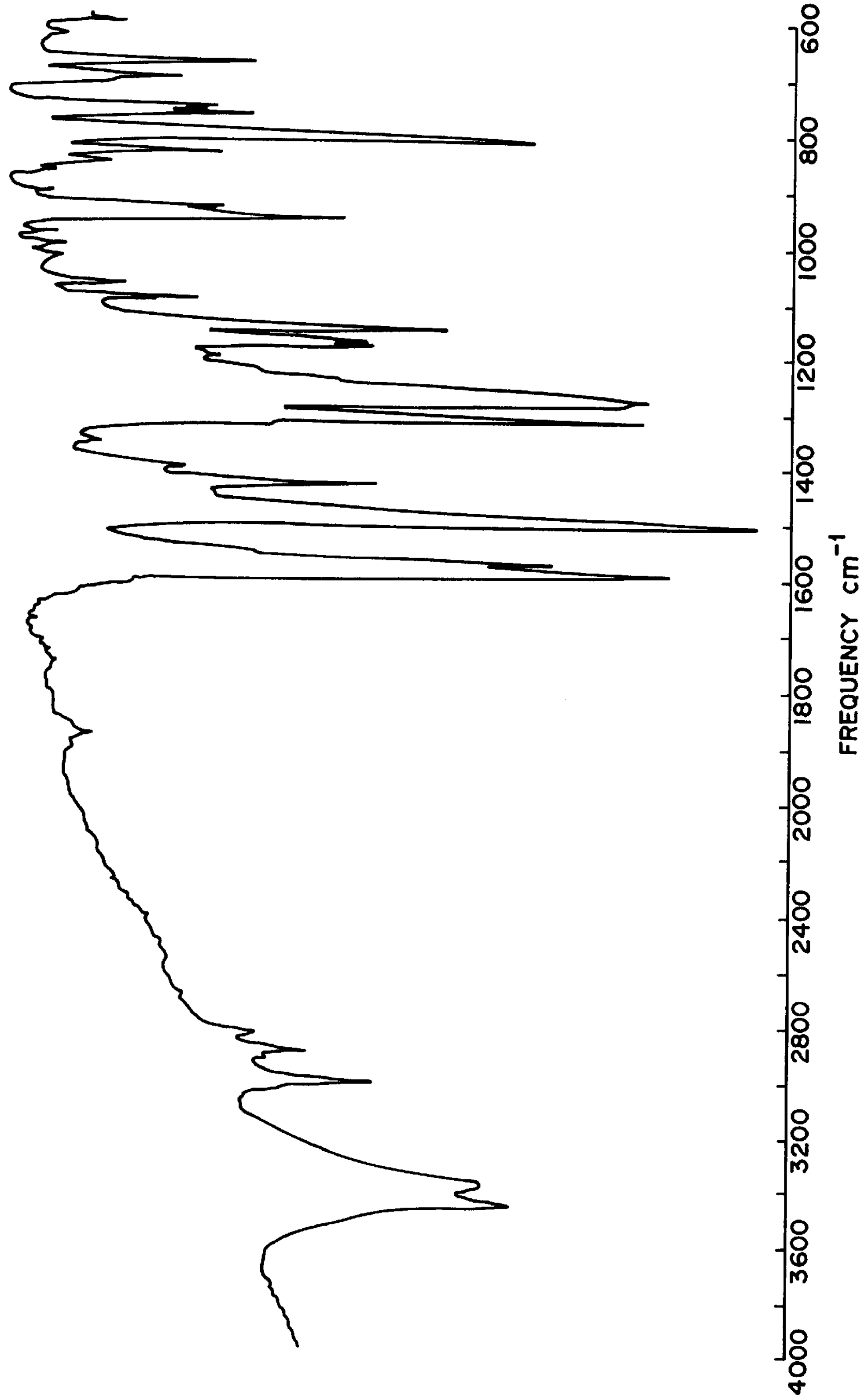
FIGS. 8 through 16 are the IR spectra of hydroxy compounds of the present invention, serving as the intermediate materials for the novel carbonate compounds, taken by use of a KBr tablet.

FIG. 8 shows an infrared spectrum of N,N-bis(4-methylphenyl)-4-amino-3'-hydroxystilbene, taken by use of a KBr tablet.

Preparation Example 1-2

[Synthesis of N-[4-(2-hydroxyethyl)phenyl]-N-(4-methylphenyl)-1-aminopyrene]

24 ml (60 mmol) of 2.5M butylithium were added to 60 ml of toluene in a stream of nitrogen, and the mixture was heated to 50° C. 60 ml of toluene solution containing 9.25 g (20.0 mmol) of N-(4-bromophenyl)-N-(4-methylphenyl)-1-aminopyrene were added dropwise to the above mixture over a period of 15 minutes, and the obtained mixture was stirred at 50° C. for 3 hours.

Thereafter, the mixture was cooled to −40° C. using a chlorobenzene - dry ice bath, and about 4.5 ml (0.1 mol) of ethylene oxide were added to the mixture. Then, the mixture was taken out of the cooling bath, so that the temperature of the mixture was returned to room temperature over a period of 3 hours. With the addition of a small amount of water to the reaction mixture, the reaction was completed.

The reaction mixture was poured into water, and the ether component was extracted from the mixture by a separating funnel. The thus obtained organic layer was washed with water, and dried over magnesium sulfate and further dried under reduced pressure, thereby producing an orange oily material.

The thus obtained material was chromatographed on a silica gel column using a mixture of toluene and ethyl acetate with a mixing ratio by volume of 10:1 as an eluting solution, and the product thus obtained was recrystallized from a mixed solvent of n-hexane and ethanol, so that N-[4-(2-hydroxyethyl)phenyl]-N-(4-methylphenyl)-1-aminopyrene of formula (III)-2 precipitated as yellow crystals in the form of scales. The yield was 4.64 g (54.3%).

(III)-2

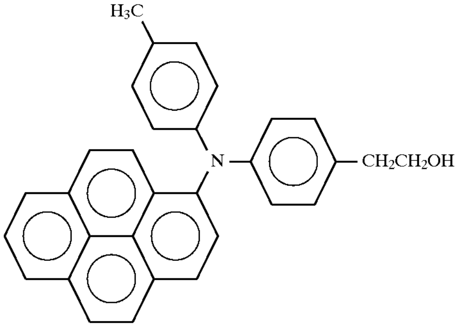

The melting point of the above hydroxy compound was 155.0° to 157.0° C.

The results of the elemental analysis of the thus obtained compound were as follows:

| | % C | % H | % N |
|---|---|---|---|
| Calculated | 87.09 | 5.89 | 3.28 |
| Found | 87.09 | 5.80 | 3.38 |

The above calculation was based on the formula for N-[4-(2-hydroxyethyl)phenyl]-N-(4-methylphenyl)-1-aminopyrene of $C_{31}H_{25}NO$.

Figure 9:
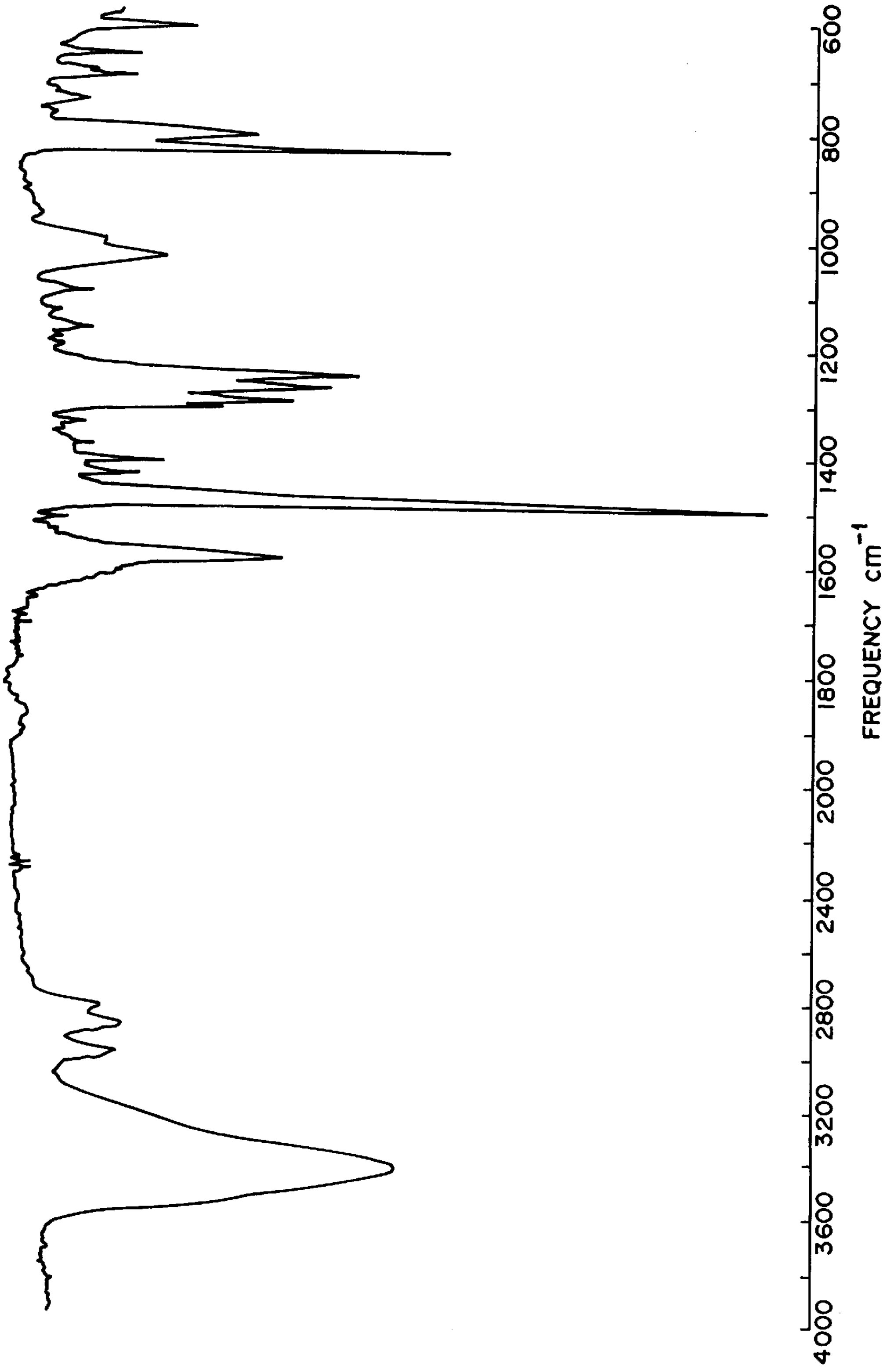
Figure 10:
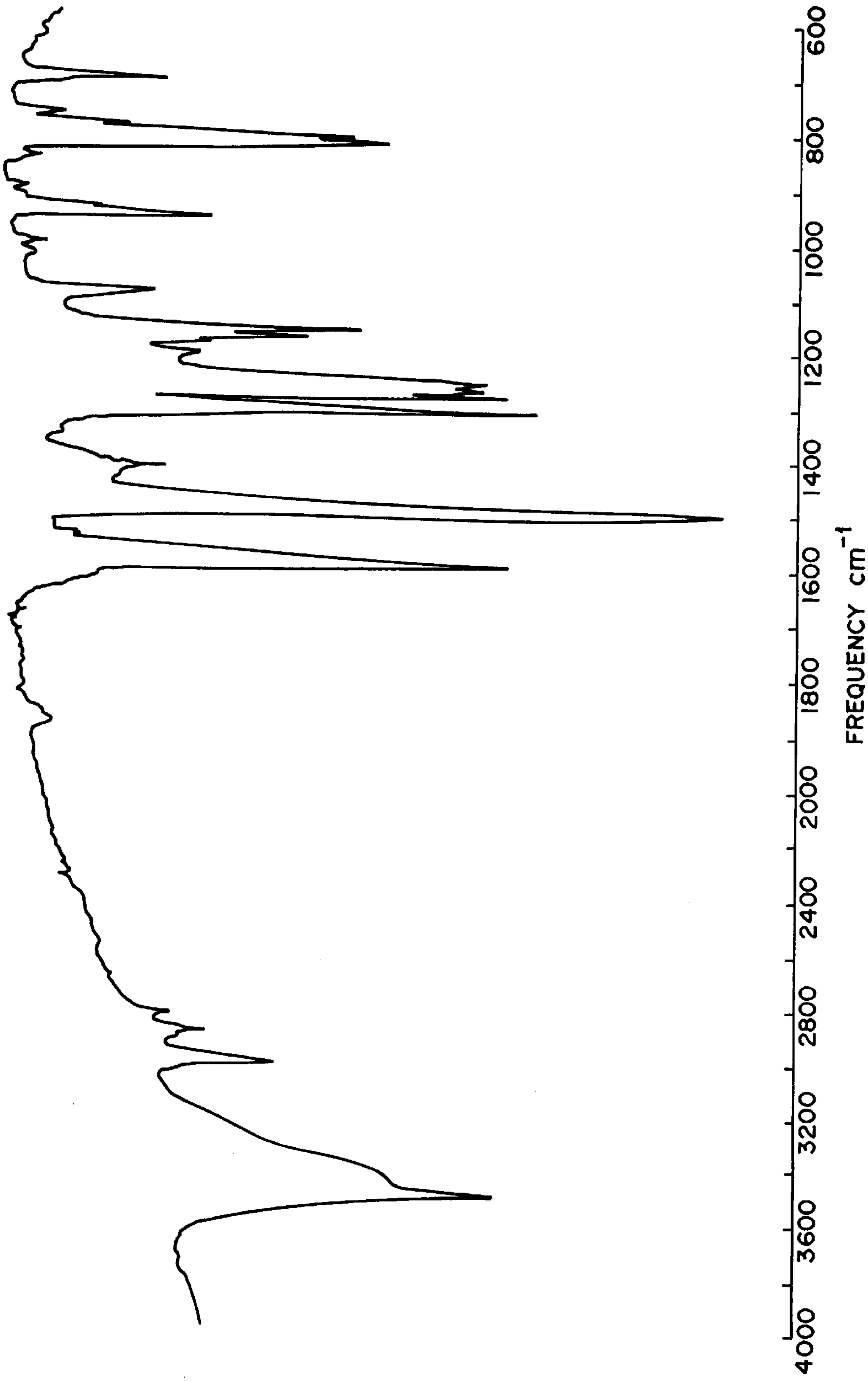
Figure 11:
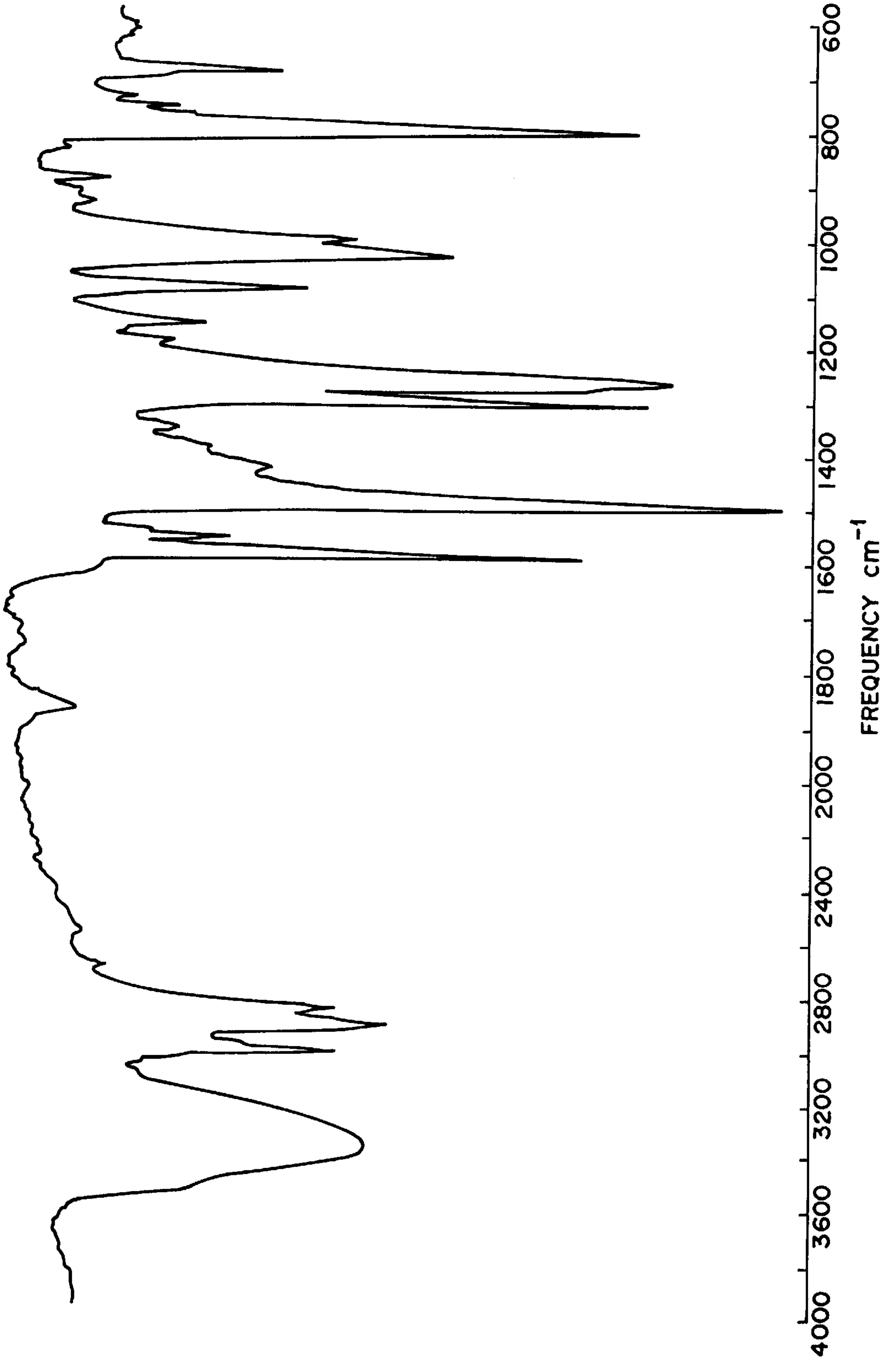
Figure 12:
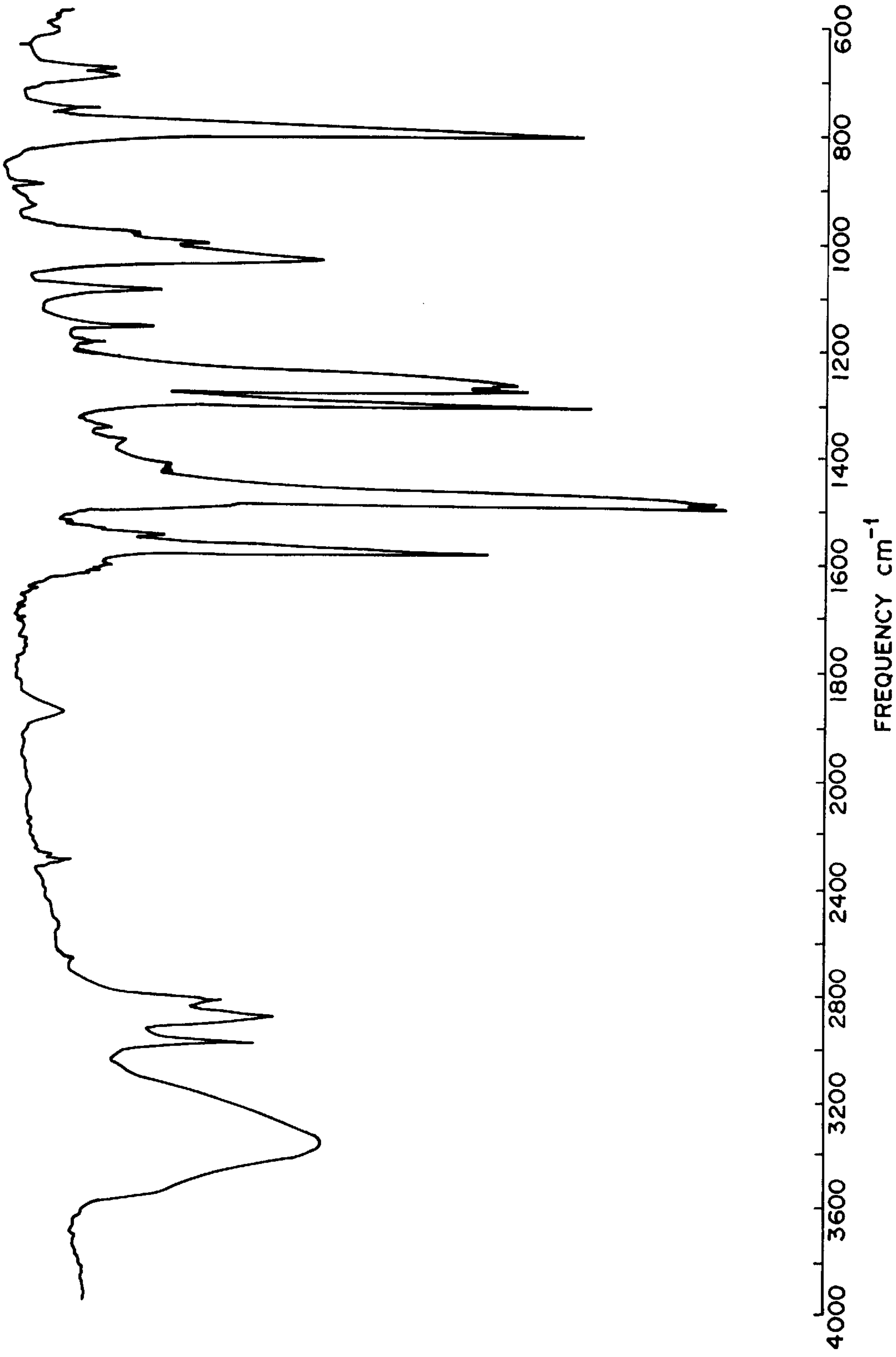
Figure 13:
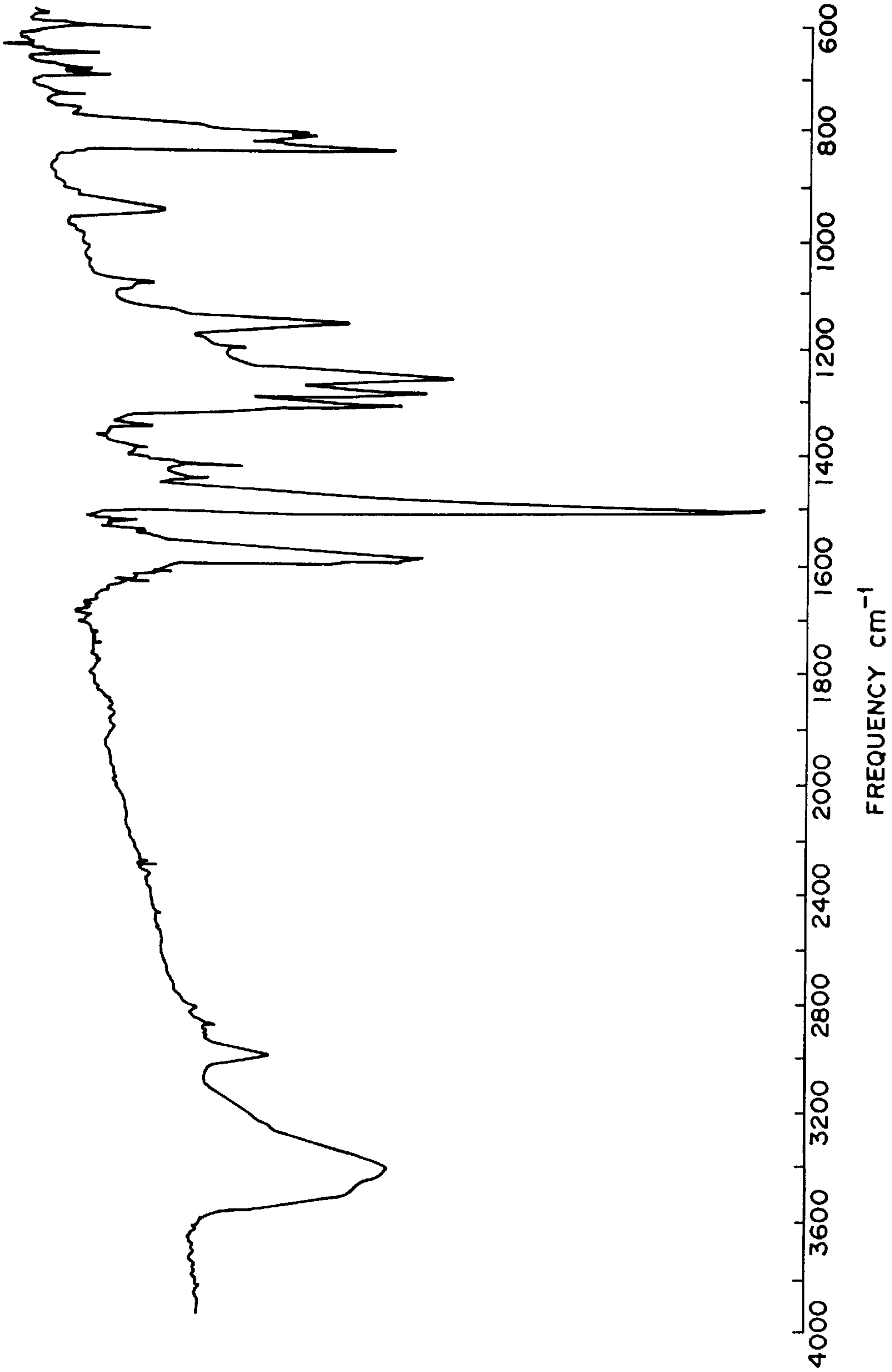
Figure 14:
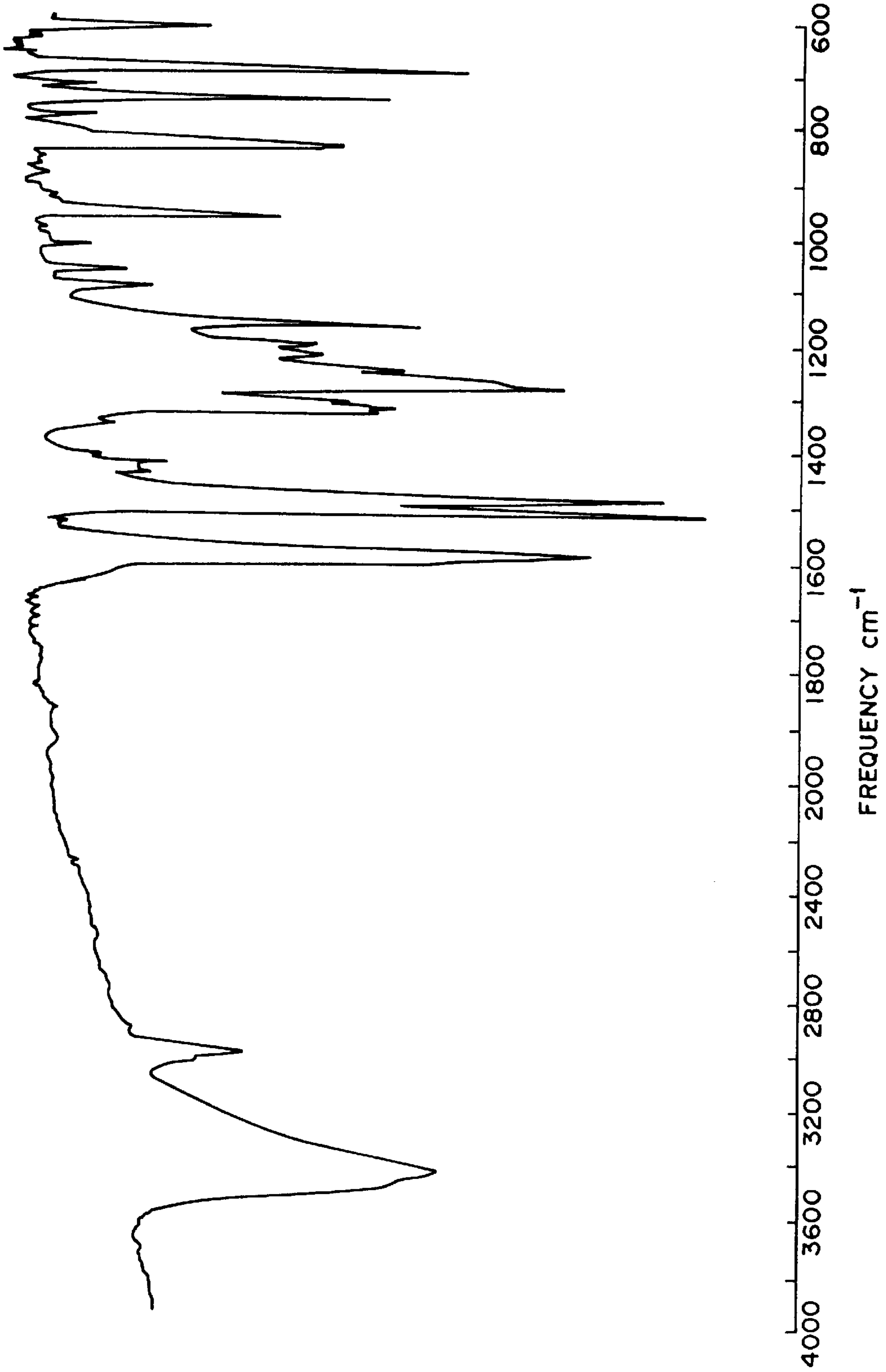
Figure 15:
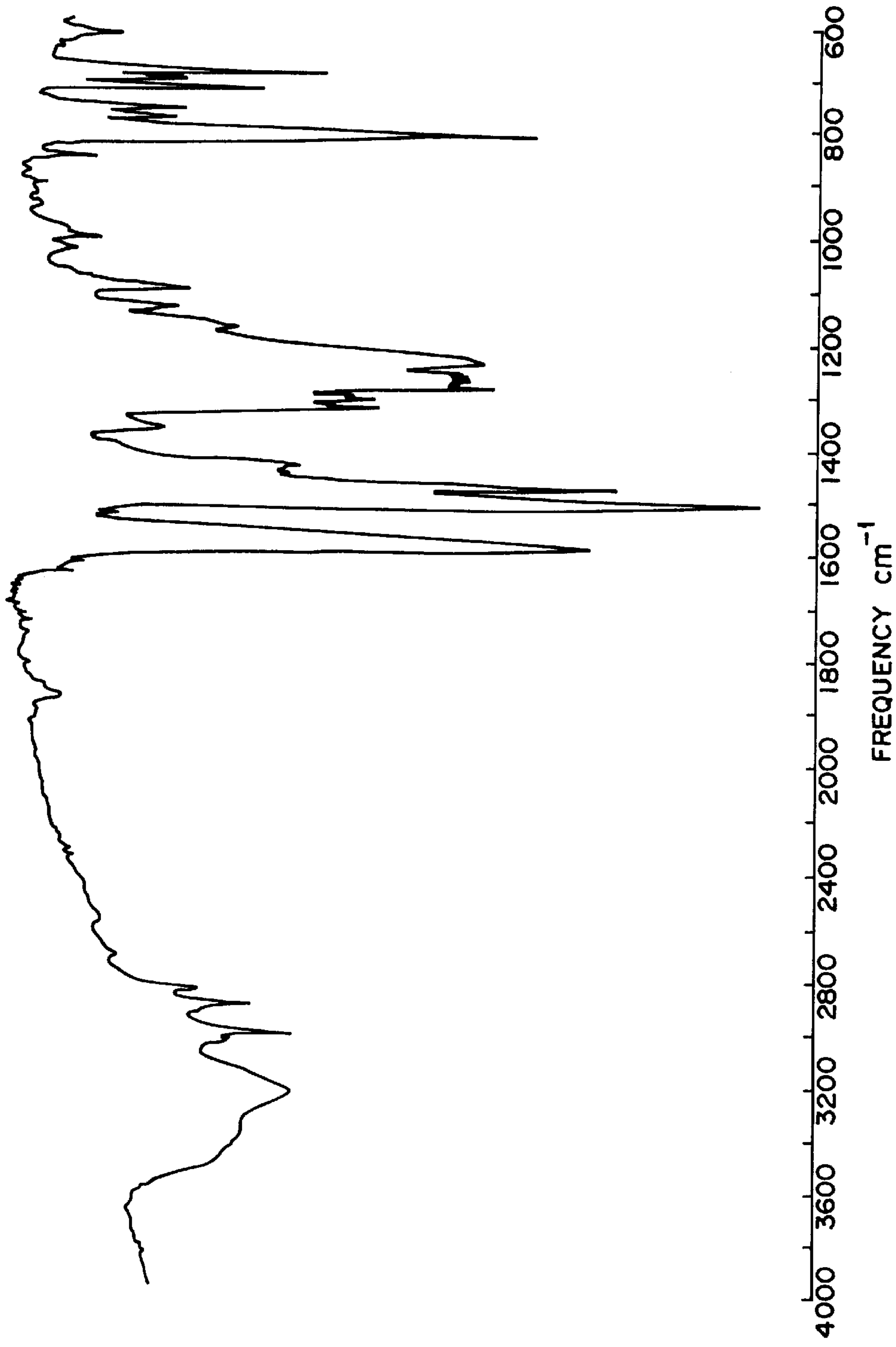
Figure 16:
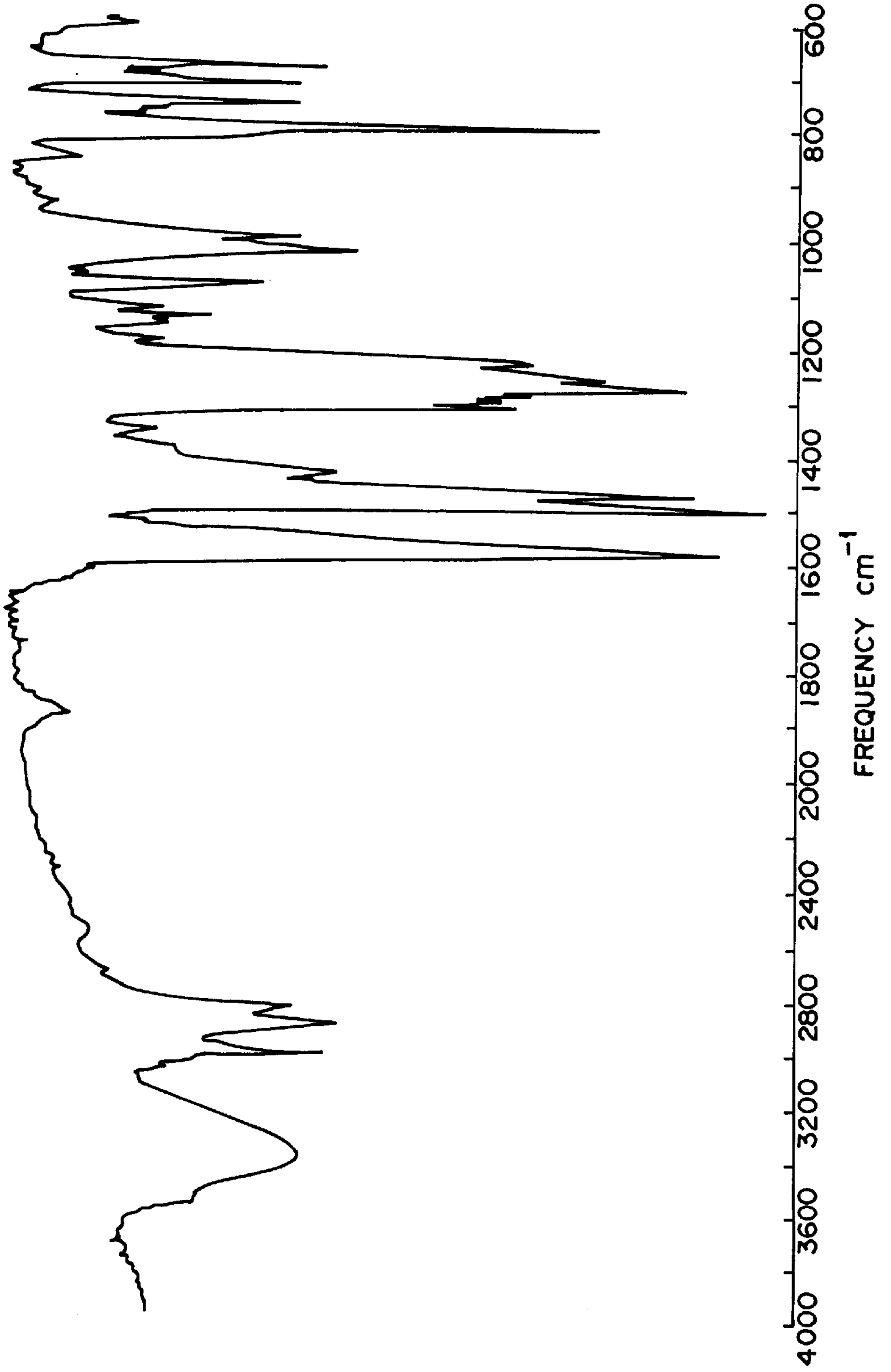

FIG. 9 shows an infrared spectrum of N-[4-(2-hydroxyethyl)phenyl]-N-(4-methylphenyl)-1-aminopyrene, taken by use of a KBr tablet.

Preparation Examples 1–3 to 1–9

A variety of hydroxy compounds were obtained in accordance with the method as described in Preparation Example 1-1 or 1-2.

The chemical formula, the melting point, and the elemental analysis of each of the obtained hydroxy compounds are shown in Table 2.

FIGS. 10 to 16 show infrared spectra of the thus obtained hydroxy compounds, taken by use of a KBr tablet.

TABLE 2
| Preparation Example No. | Chemical Formula | Melting Point (°C.) | Elemental Analysis (Calculated) Found % C | % H | % N |
|---|---|---|---|---|---|
| 1-3 | 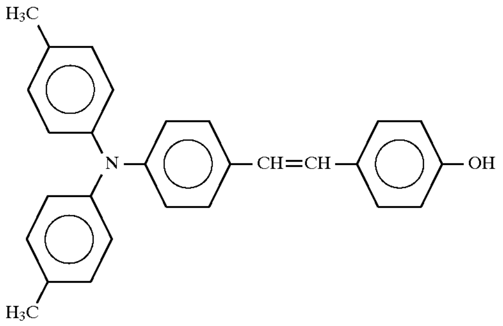 | 159.5–161.0 | (86.90) 86.29 | (6.44) 6.70 | (3.58) 3.48 |
| 1-4 | 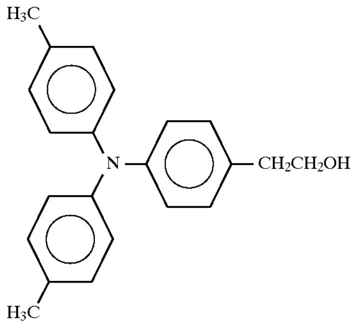 | amorphous | (83.24) 83.20 | (7.30) 7.41 | (4.41) 4.27 |
| 1-5 | 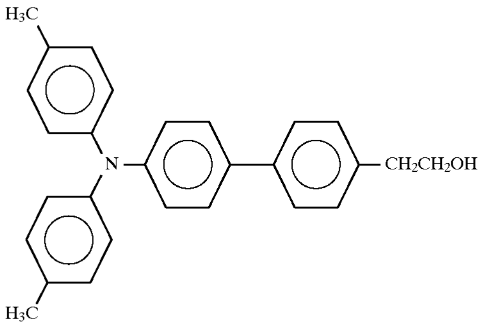 | 88.0–91.0 | (85.46) 85.08 | (6.92) 6.85 | (3.56) 3.50 |
| 1-6 | 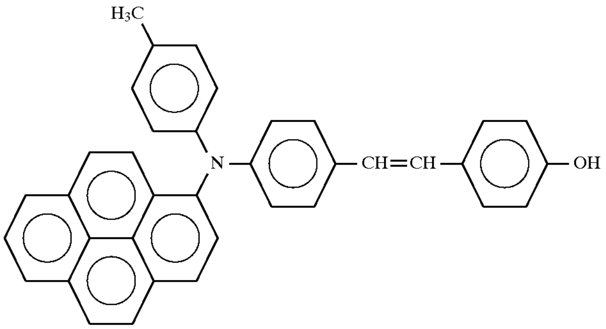 | 160 | (88.69) 88.69 | (5.43) 5.37 | (2.79) 2.73 |

TABLE 2-continued

| Preparation Example No. | Chemical Formula | Melting Point (°C.) | Elemental Analysis (Calculated) Found % C | % H | % N |
|---|---|---|---|---|---|
| 1-7 | 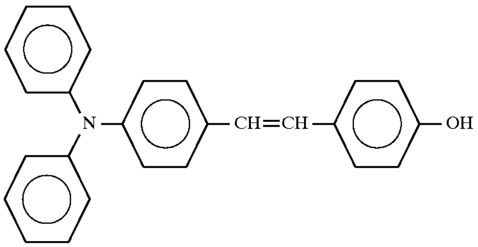 | 185.5–186.5 | (85.92) 85.82 | (5.82) 5.85 | (3.85) 3.81 |
| 1-8 | 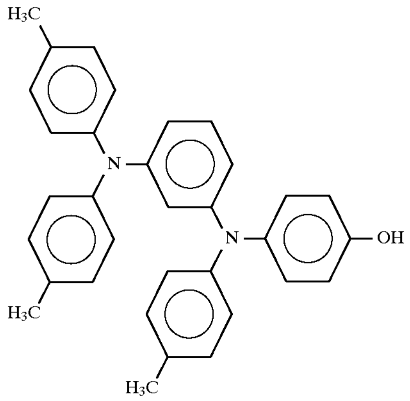 | 99.5–103.5 | (84.22) 84.48 | (6.43) 6.46 | (5.95) 5.95 |
| 1-9 | 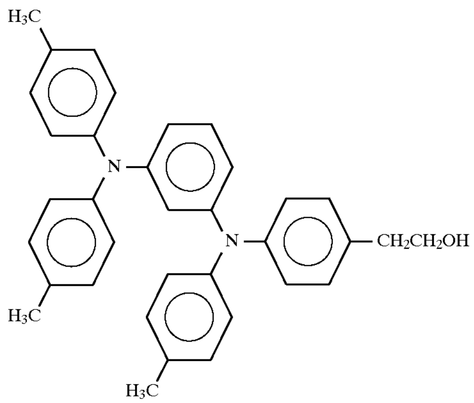 | 112.5–115.6 | (84.30) 84.59 | (6.87) 6.89 | (5.62) 5.65 |

Preparation Example 2-1

[Synthesis of a carbonate compound]

3.66 g (10.0 mmol) of N,N-bis(4-methylphenyl)-4'-hydroxy-4-biphenylamine and 1.55 g (12.0 mmol) of quinoline were dissolved in 15 ml of dichloromethane. 10 ml of dichloromethane solution containing 1.72 g (11.0 mmol) of phenyl chloroformate were added dropwise to the above prepared mixture at room temperature in a stream of nitrogen over a period of 15 minutes, and the reaction mixture was stirred for 3.5 hours.

After the completion of the reaction, the reaction mixture was washed with water using a separating funnel, and dried over magnesium sulfate and further dried under reduced pressure, thereby producing a pale green oily material.

The thus obtained material was chromatographed on a silica gel column using a mixture of toluene and n-hexane with a mixing ratio by volume of 3:1 as an eluting solution, and the product thus obtained was recrystallized from a mixed solvent of ethyl acetate and methanol, so that a carbonate compound of formula (II)-1 precipitated as colorless crystals in the form of needles. The yield was 3.24 g (66.7%).

(II)-1

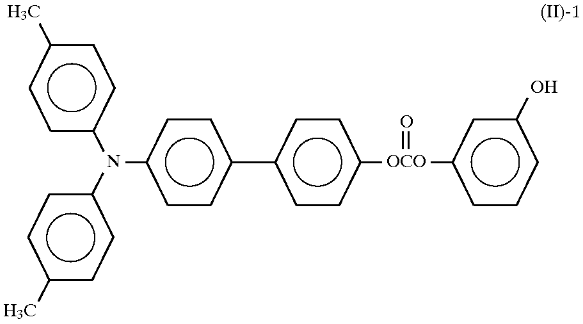

The melting point of the above carbonate compound was 88.0° to 91.0° C.

| | % C | % H | % N |
|---|---|---|---|
| Calculated | 81.96 | 5.21 | 2.90 |
| Found | 82.21 | 5.18 | 2.91 |

Figure 7:
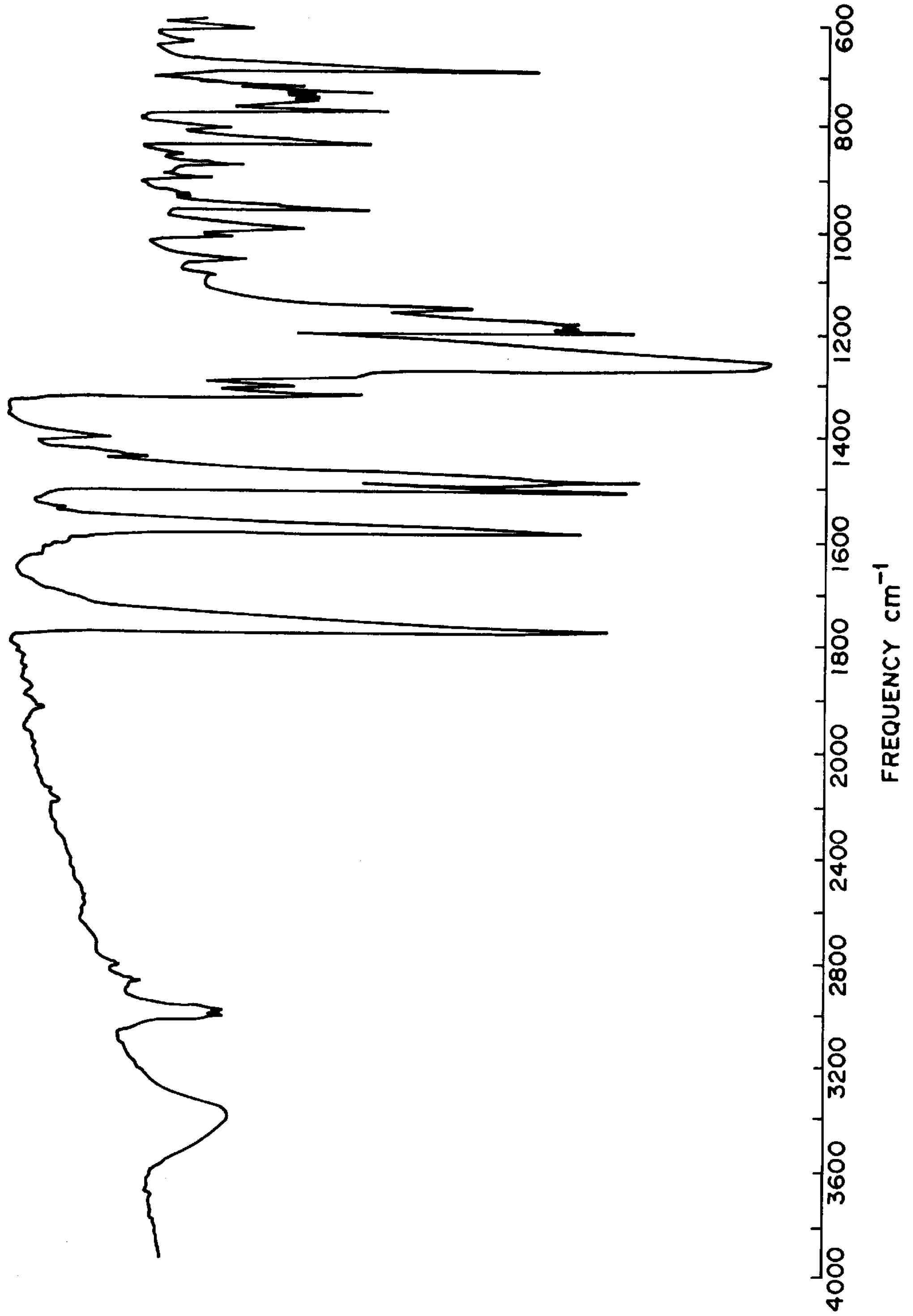

FIG. 7 shows an infrared spectrum of the above prepared carbonate compound, taken by use of a KBr tablet.

Application Example 2-1

N,N-bis(4-methylphenyl)-4-amino-3'-hydroxystilbene of formula (III)-1 synthesized in Preparation Example 1-1 was allowed to react with bis(chloroformate) of formula (V)-2, so that a carbonate compound of formula (II') was obtained.

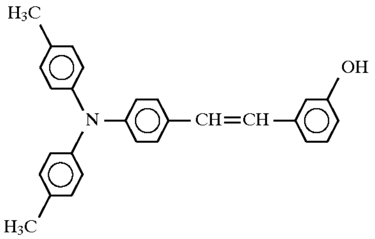

(III)-1

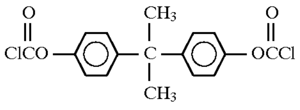

(V)-2

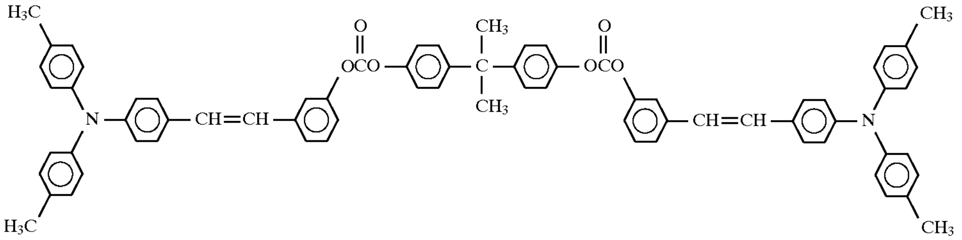

(II')

The results of the elemental analysis of the thus obtained carbonate compound were as follows:

| | % C | % H | % N |
|---|---|---|---|
| Calculated | 81.62 | 5.61 | 2.89 |
| Found | 82.04 | 5.62 | 3.01 |

The above calculation was based on the formula for the carbonate compound of $C_{33}H_{27}NO_3$.

Figure 6:
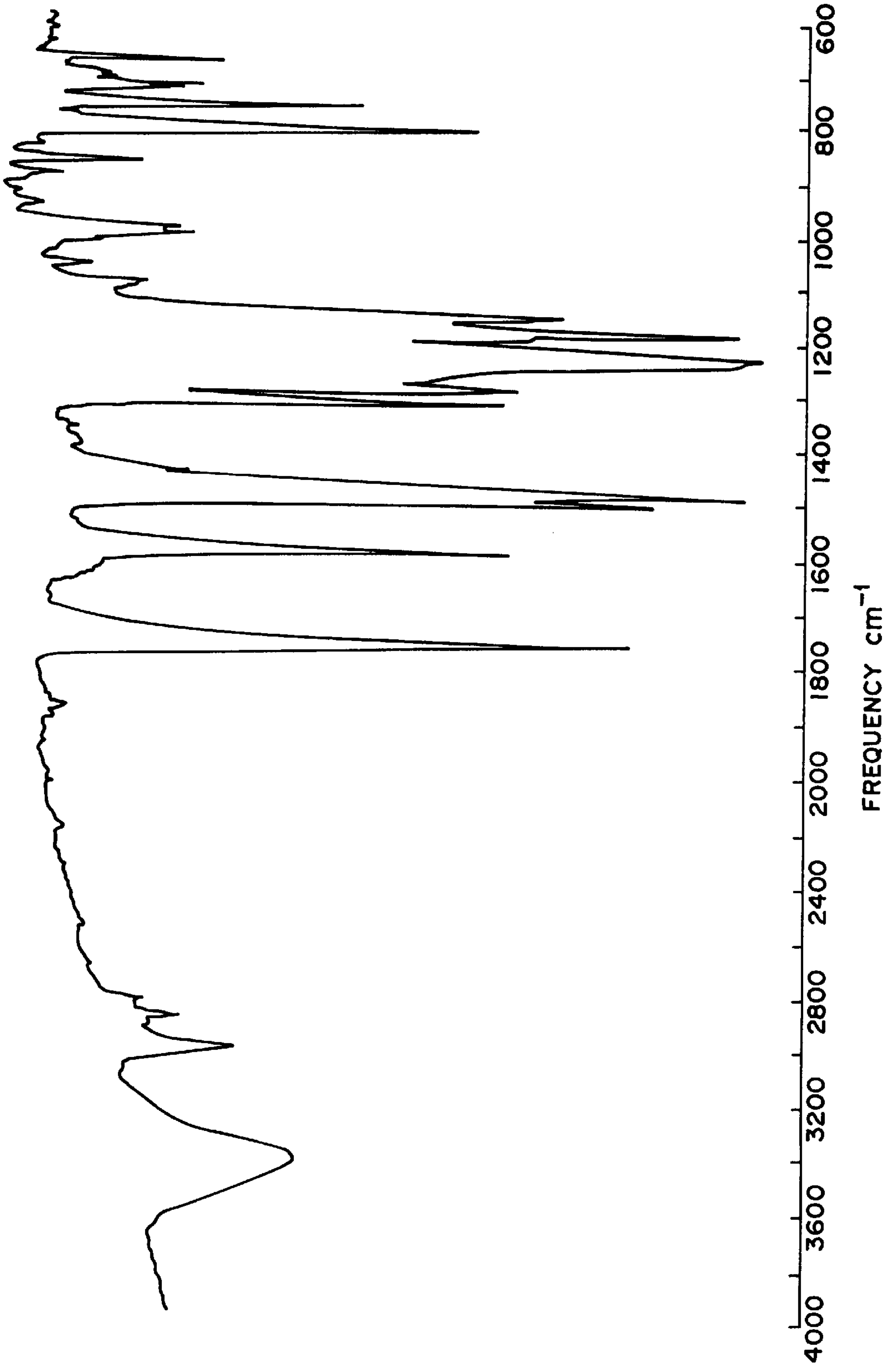
FIGS. 6 and 7 are the IR spectra of carbonate compounds according to the present invention, taken by use of a KBr tablet.

FIG. 6 shows an infrared spectrum of the above prepared carbonate compound, taken by use of a KBr tablet.

Preparation Example 2-2

A carbonate compound of formula (II)-2 was obtained in accordance with the method as described in Preparation Example 2-1.

(II)-2

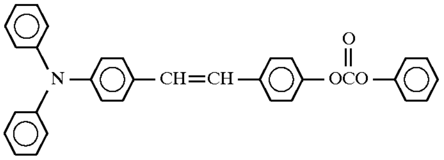

The melting point of the above carbonate compound was 136.0° to 137.0° C.

The results of the elemental analysis of the thus obtained carbonate compound were as follows:

EXAMPLE 1

76 parts by weight of Diane Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

2 parts by weight of the carbonate compound No. 9 in Table 1 prepared in the above-mentioned Preparation Example 2-2, 2 parts by weight of polycarbonate resin (Trademark "Panlite K-1300" made by Teijin Limited.) and 16 parts by weight of tetrahydrofuran were mixed to form a coating solution for a charge transport layer. This coating solution was coated on the above formed charge generation layer by a doctor blade and then dried at 80° C. for 2 minutes and then at 120° C. for 5 minutes, so that a charge transport layer having a thickness of about 20 μm was formed on the charge generation layer.

Thus, a two-layered electrophotographic photoconductor No. 1 according to the present invention was prepared.

EXAMPLES 2 TO 27 AND 32 TO 34

The procedure for preparation of the two-layered electrophotographic photoconductor No. 1 in Example 1 was repeated except that Diane Blue serving as a charge generating material and the carbonate compound No. 9 serving as a charge transporting material employed in Example 1 were replaced by the respective charge generating materials and charge transporting materials listed in the following Table 3, whereby two-layered electrophotographic photoconductors No. 2 to No. 27 and No. 32 to No. 34 according to the present invention were prepared.

TABLE 3
| Photoconductor No. | Charge Generating Material | Charge Transporting Material (Carbonate Compound No.) |
|---|---|---|
| 1 | 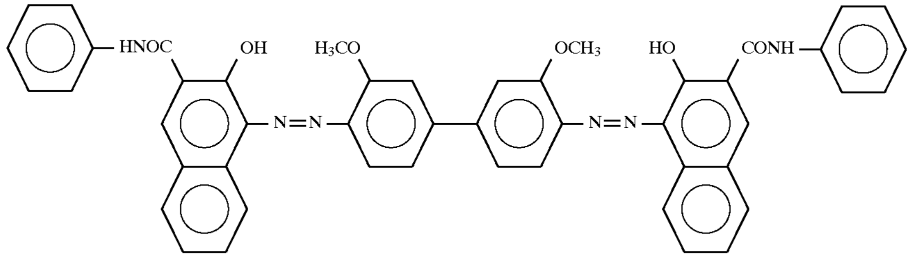 | 9 |
| 2 | 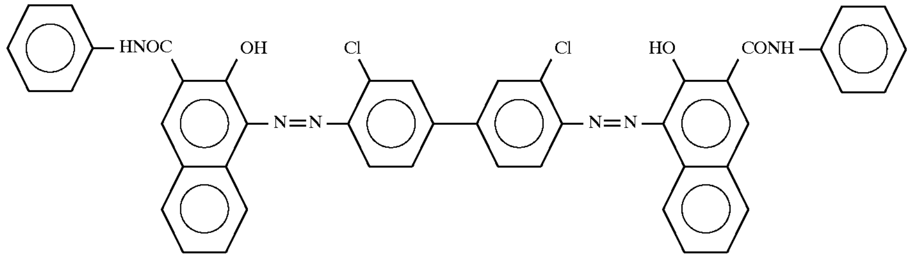 | 9 |
| 3 | 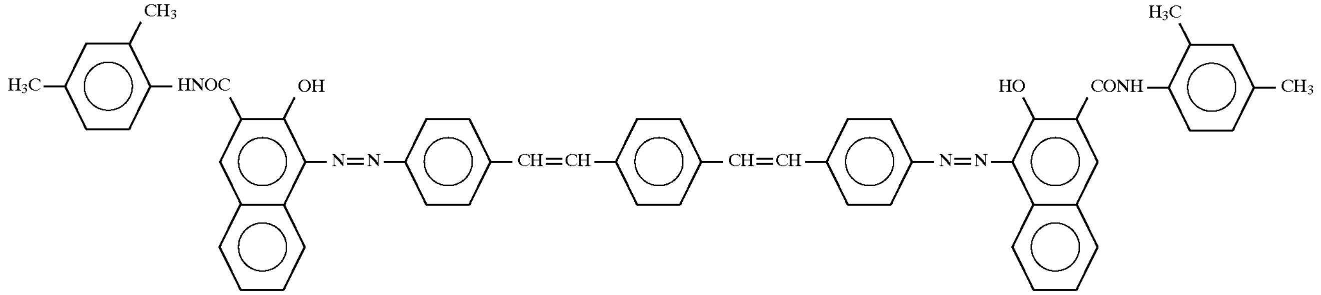 (hereinafter referred to as P-1.) | 9 |

TABLE 3-continued
| Photoconductor No. | Charge Generating Material | Charge Transporting Material (Carbonate Compound No.) |
|---|---|---|
| 4 | 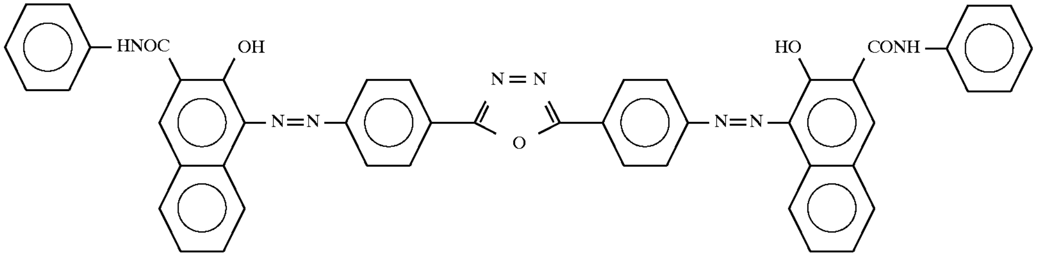 | 9 |
| 5 | 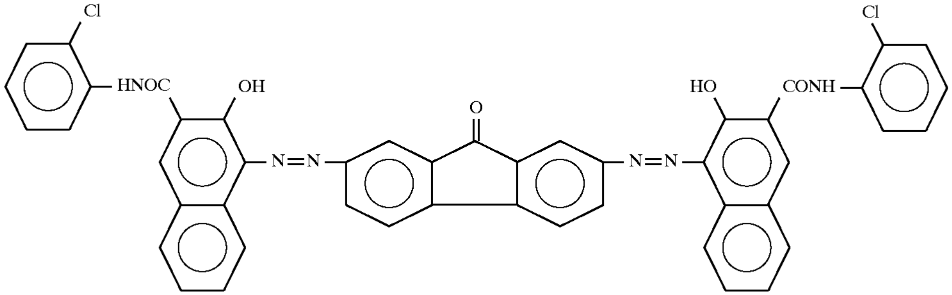 (hereinafter referred to as P-2.) | 9 |
| 6 | 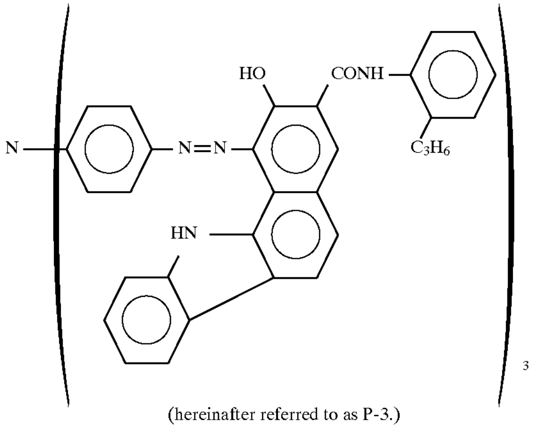 (hereinafter referred to as P-3.) | 9 |

TABLE 3-continued
| Photoconductor No. | Charge Generating Material | Charge Transporting Material (Carbonate Compound No.) |
|---|---|---|
| 7 | β-type Copper Phthalocyanine | 9 |
| 8 | 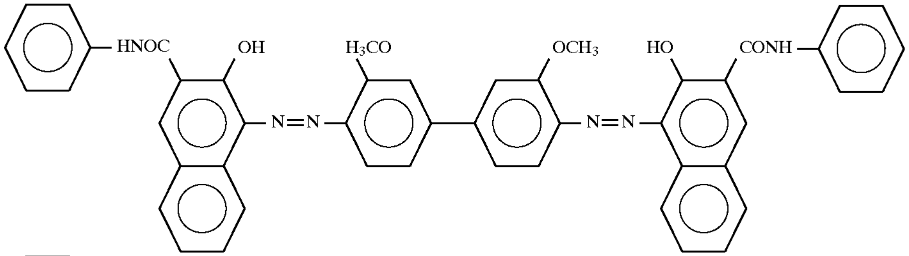 | 14 |
| 9 | 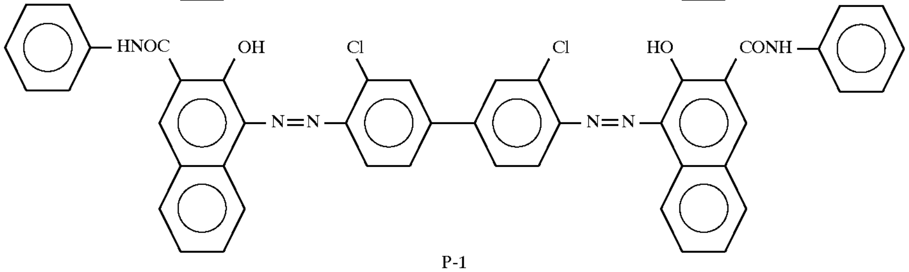 | 14 |
| 10 | P-1 | 14 |
| 11 | P-2 | 14 |
| 12 | P-3 | 14 |
| 13 | P-1 | 19 |
| 14 | P-2 | 19 |
| 15 | P-3 | 19 |
| 16 | P-1 | 26 |
| 17 | P-2 | 26 |
| 18 | P-3 | 26 |
| 19 | P-1 | 32 |
| 20 | P-2 | 32 |
| 21 | P-3 | 32 |
| 22 | P-1 | 33 |
| 23 | P-2 | 33 |
| 24 | P-3 | 33 |
| 25 | P-1 | 43 |
| 26 | P-2 | 43 |
| 27 | P-3 | 43 |
| 32 | P-1 | 12 |
| 33 | P-2 | 12 |
| 34 | P-3 | 12 |

EXAMPLE 28

Selenium was vacuum-deposited on an aluminum plate having a thickness of about 300 μm, so that a charge generation layer having a thickness of about 1 μm was formed on the aluminum plate.

2 parts by weight of the carbonate compound No. 9 in Table 1 prepared in the above-mentioned Preparation Example 2-2, 3 parts by weight of polyester resin (Trademark "Polyester Adhesive 49000" made by Du Pont de Nemours, E.I. & Co.) and 45 parts by weight of tetrahydrofuran were mixed to form a coating liquid for a charge transport layer. This coating liquid was coated on the above formed charge generation layer by a doctor blade, dried at room temperature, and then dried under reduced pressure, so that a charge transport layer with a thickness of about 10 μm was formed on the charge generation layer.

Thus, a two-layered electrophotographic photoconductor No. 28 according to the present invention was prepared.

EXAMPLE 29

The procedure for preparation of the two-layered electrophotographic photoconductor No. 28 in Example 28 was repeated except that a charge generation layer with a thickness of about 0.6 μm was formed on the same aluminum plate as employed in Example 28 by deposition of a perylene pigment of formula (A) instead of selenium, so that a two-layered electrophotographic photoconductor No. 29 according to the present invention was prepared.

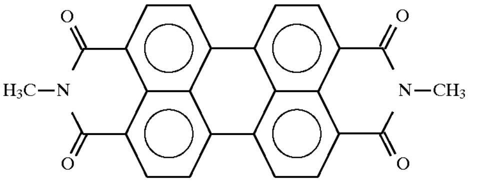
(A)

EXAMPLE 30

A mixture of one part by weight of the same Diane Blue as employed in Example 1 and 158 parts by weight of tetrahydrofuran was dispersed and ground in a ball mill to form a dispersion. To the thus formed dispersion, 12 parts by weight of the carbonate compound No. 9 in Table 1 and 18 parts by weight of polyester resin (Trademark "Polyester Adhesive 49000" made by Du Pont de Nemours, E.I. & Co.) were added to form a coating liquid for a photoconductive layer. This coating liquid was coated on an aluminum surface of an aluminum-deposited polyester film by a doctor blade, and dried at 100° C. for 30 minutes, so that a photoconductive layer having a thickness of about 16 μm was formed on the electroconductive support.

Thus, an electrophotographic photoconductor No. 30 according to the present invention was prepared.

EXAMPLE 31

2 parts by weight of the carbonate compound No. 9 in Table 1 prepared in the above-mentioned Preparation Example 2-1, 2 parts by weight of polycarbonate resin (Trademark "Panlite K-1300" made by Teijin Limited.) and 16 parts by weight of a tetrahydrofuran were mixed to form a coating liquid for a charge transport layer. This coating liquid was coated on an aluminum surface of an aluminum-deposited polyester film by a doctor blade and dried at 80° C. for 2 minutes, and then at 120° C. for 5 minutes, so that a charge transport layer with a thickness of about 20 μm was formed on the aluminum-deposited polyester film.

A mixture of 13.5 parts by weight of the bisazo pigment (P-2) shown in Table 3, 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill. To this dispersion, 1700 parts by weight of additional ethyl cellosolve were added to form a coating liquid for a charge generation layer. This coating liquid was coated on the above formed charge transport layer by spray coating and dried at 100° C. for 10 minutes, so that a charge generation layer having a thickness of about 0.2 μm was formed on the charge transport layer.

A methanol - n-butanol solution of a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer.

Thus, an electrophotographic photoconductor No. 31 according to the present invention was prepared.

Application Example 1

7.5 parts by weight of a bisazo compound of formula (B) serving as a charge generating material and 500 parts by weight of a 0.5% tetrahydrofuran solution of a polyester resin (Trademark "Vylon 200" made by Toyobo Company, Ltd.) were dispersed and ground in a ball mill.

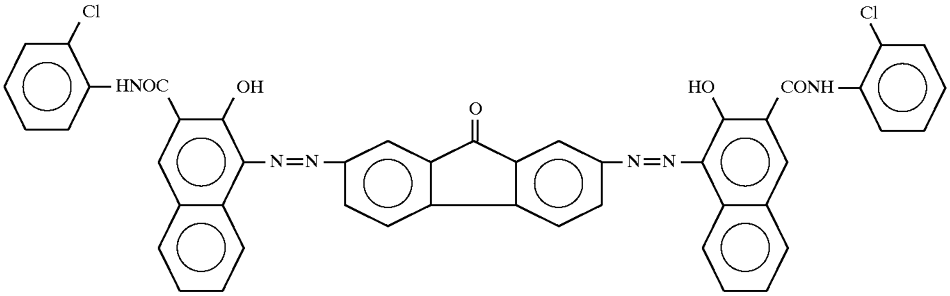
(B)

The thus obtained dispersion was coated on an aluminum surface of an aluminum-deposited polyester film by a doctor blade, and dried at room temperature, so that a charge generation layer having a thickness of about 1 μm was formed on the aluminum-deposited polyester film.

One part by weight of the carbonate compound of formula (II') synthesized in Application Example 2-1 was dissolved in a resin solution prepared by dissolving one part by weight of polycarbonate resin (Trademark "Panlite K-1300" made by Teijin Limited.) in 8 parts by weight of tetrahydrofuran, so that a coating liquid for a charge transport layer was obtained. This coating liquid was coated on the above formed charge generation layer by a doctor blade and then dried at 80° C. for 2 minutes, and at 120° C. for 5 minutes, so that a charge transport layer having a thickness of about 20 μm was formed on the charge generation layer.

Thus, a two-layered electrophotographic photoconductor was prepared.

Each of the electrophotographic photoconductors No. 1 through No. 34 according to the present invention prepared in Examples 1 to 34 and the photoconductor prepared in Application Example 1 was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photo-conductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux·sec) required to reduce the initial surface potential Vpo (V) to ½ the initial surface potential Vpo (V) was measured. The results are shown in Table 4.

TABLE 4

| Photoconductor No. | Vpo (V) | $E_{1/2}$ (lux.sec) |
|---|---|---|
| 1 | −1256 | 1.60 |
| 2 | −1311 | 1.56 |
| 3 | −1482 | 1.43 |
| 4 | −1551 | 1.62 |
| 5 | −1478 | 1.45 |
| 6 | −1428 | 1.24 |
| 7 | −1321 | 1.50 |
| 8 | −1388 | 1.58 |
| 9 | −1295 | 1.62 |
| 10 | −1382 | 1.14 |
| 11 | −1410 | 1.08 |
| 12 | −1091 | 1.09 |
| 13 | −1366 | 1.40 |
| 14 | −1451 | 1.46 |
| 15 | −1309 | 1.28 |
| 16 | −1457 | 1.10 |
| 17 | −1488 | 1.09 |
| 18 | −1025 | 0.96 |
| 19 | −1521 | 1.49 |
| 20 | −1081 | 1.50 |
| 21 | −926 | 1.33 |
| 22 | −1516 | 1.48 |
| 23 | −1499 | 1.46 |
| 24 | −1021 | 1.29 |
| 25 | −1511 | 1.52 |
| 26 | −1333 | 1.40 |
| 27 | −1310 | 1.26 |
| 28 | −1425 | 1.60 |
| 29 | −921 | 1.65 |
| 30 | +1321 | 1.80 |
| 31 | +1480 | 1.47 |
| 32 | −1482 | 1.31 |
| 33 | −1441 | 1.29 |
| 34 | −1073 | 0.78 |
| Application Example 1 | −1422 | 1.50 |

EXAMPLE 35

The procedure for preparation of the electrophotographic photoconductor as in Application Example 1 was repeated except that the carbonate compound (II') for use in the coating liquid for the charge transport layer in Application Example 1 was replaced by the carbonate compound (II)-1 synthesized in Preparation Example 2-1.

Thus, a two-layered electrophotographic photoconductor No. 35 according to the present invention was prepared.

The thus prepared electrophotographic photoconductor No. 35 according to the present invention was charged negatively in the dark under application of −6 kV of corona charge for 20 seconds, using a commercially available electrostatic copying sheet testing apparatus ("Paper Analyzer Model SP-428" made by Kawaguchi Electro Works Co., Ltd.). The initial surface potential Vm (V) of the photoconductor was measured. Then, the photoconductor was allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{1/2}$ (lux·sec) required to reduce the initial surface potential Vpo (V) to ½ the initial surface potential Vpo (V) was measured. Furthermore, the surface potential Vr (V) of the photoconductor was measured after exposed to the tungsten lamp for 30 seconds. The results are as follows:

Vm (V): −1619

Vpo (V): −1478

Vr (V): 0

$E_{1/2}$: 1.45

Furthermore, each of the above obtained electrophotographic photoconductors No. 1 to No. 36 was set in a commercially available electrophotographic copying machine, and the photoconductor was charged and exposed to light images via the original images to form latent electrostatic images thereon. Then, the latent electrostatic images formed on the photoconductor were developed into visible toner images by a dry developer, and the visible toner images were transferred to a sheet of plain paper and fixed thereon. As a result, clear toner images were obtained on the paper. When a wet developer was employed for the image formation, clear images were formed on the paper similarly.

The photoconductive layer of the electrophotographic photoconductor according to the present invention comprises as the photoconductive material at least one carbonate compound of formula (I) or (II), so that not only the photoconductive properties of the photoconductor can be improved, but also the resistance to heat and mechanical shocks of the photoconductor can be increased. Furthermore, the photoconductors according to the present invention can be manufactured at low cost.

Japanese Patent Application No. 05-168523 filed on Jun. 15, 1993, Japanese Patent Application No. 05-217032 filed on Aug. 9, 1993, Japanese Patent Application No. 05-171155 filed on Jun. 17, 1993, Japanese Patent Application No. 05-288701 filed on Oct. 25, 1993, Japanese Patent Application No. 05-171156 filed on Jun. 17, 1993, and Japanese Patent Application No. 05-217031 filed on Aug. 9, 1993 are hereby incorporated by reference.

What is claimed is:

1. A hydroxy compound of formula (III'):

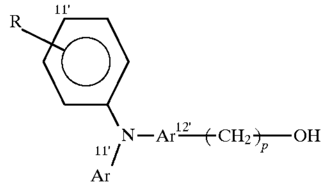

(III')

wherein $R^{11'}$ is hydrogen, an alkyl group, an alkoxyl group, a phenyl group which may be substituted by an alkyl group, or a diphenylamino group which may be substituted by an alkyl group; $Ar^{11'}$ is a phenyl group which may be substituted by an alkyl group, a biphenylyl group which may be substituted by an alkyl group, or a condensed polycyclic group; $Ar^{12'}$ is phenylene group, a biphenylene group, or a bivalent stilbene group; and p is an integer of 0 to 2, excluding hydroxy compounds of formula (III') where the following are satisfied at the same time: $R^{11'}$ is hydrogen or an alkyl group, $Ar^{11'}$ is phenyl group which may have an alkyl group as a substituent, $Ar^{12'}$ is as phenylene group and p is 0 or 1; and excluding hydroxy compounds of formula (III') where the following are satisfied at the same time: $R^{11'}$ is an alkoxy group, $Ar^{11'}$ is a phenyl group, $Ar^{12}$ is a bivalent arylene group and p is 0.

2. A hydroxy compound of formula (III):

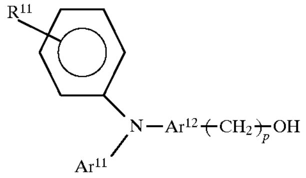

(III)

wherein $R^{11}$ is hydrogen, an alkyl group, an alkoxyl group, a phenyl group which may have a substituent, or a vinyl group which may have a substituent; $Ar^{11}$ is selected from the group consisting of a naphthyl group, an anthryl group, a pyrenyl group, a methylphenyl group, a methoxyphenyl group, a biphenylyl group, a methylbiphenyl group and a methoxybiphenyl group; $Ar^{12}$ is a bivalent arylene group, a bivalent stilbene which may have a substituent, or a bivalent 1,2-diphenylethane which may have a substituent; and p is an integer of 0 to 2, excluding hydroxy compounds of formula (III) where the following are satisfied at the same time: $R^{11}$ is hydrogen or an alkyl group; $Ar^{11}$ is a phenyl group which may have an alkyl group as a substituent; $Ar^{12}$ is a phenylene group; and p is 0 or 1; and excluding hydroxy compounds of formula (III) where the following are satisfied at the same time: $R^{11}$ is an alkoxyl group; $Ar^{11}$ is a phenyl group; $Ar^{12}$ is a bivalent arylene group; and p is 0.

3. The hydroxy compound of claim 2, wherein $R^{11}$ is selected from the group consisting of a methyl group, an ethyl group, a propyl group, a butyl group, a methoxy group, an ethoxy group, a propoxy group, a butoxy group, a styryl group, a β-phenylstyryl group, a β-methylstyryl group, a methylphenyl group, a methoxyphenyl group, a biphenylyl group, a methylbiphenyl group and a methoxybiphenyl group.

4. The hydroxy compound of claim 1, wherein $R^{11}$ is selected from the group consisting of a methyl group, an ethyl group, a propyl group, a butyl group, a methoxy group, an ethoxy group, a propoxy group, a butoxy group, a styryl group, a β-phenylstyryl group, a β-methylstyryl group, a methylphenyl group, a methoxyphenyl group, a biphenylyl group, a methylbiphenyl group and a methoxybiphenyl group.

5. The hydroxy compound of claim 1, wherein $Ar^{11}$ is selected from the group consisting of a naphthyl group, an anthryl group, a pyrenyl group, a methylphenyl group, a methoxyphenyl group, a biphenylyl group, a methylbiphenyl group and a methoxybiphenyl group.

6. The hydroxy compound of claim 1, wherein $Ar^{12}$ is selected from the group consisting of a phenylene group, a biphenylene group, a bivalent α-phenylstilbene, and a bivalent α-methylstilbene.

7. A hydroxy compound of formula (III):

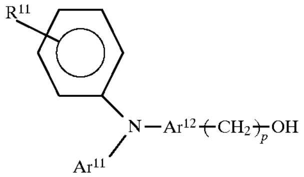

(III)

wherein $R^{11}$ is hydrogen, an alkyl group, an alkoxyl group, a phenyl group which may have a substituent, or a vinyl group which may have a substituent; $Ar^{11}$ is a phenyl group which may have a substituent, or a condensed polycyclic group; $Ar^{12}$ is selected from the group consisting of a phenylene group, a biphenylene group, a bivalent α-phenylstilbene, a bivalent α-methylstilbene and 1,1,2-triphenylethane; and p is an integer of 0 to 2, excluding hydroxy compounds of formula (III) where the following are satisfied at the same time: $R^{11}$ is hydrogen or an alkyl group; $Ar^{11}$ is a phenyl group which may have an alkyl group as a substituent; $Ar^{12}$ is a phenylene group; and p is 0 or 1; and excluding hydroxy compounds of formula (III) where the following are satisfied at the same time: $R^{11}$ is an alkoxyl group; $Ar^{11}$ is a phenyl group; $Ar^{12}$ is a bivalent arylene group; and p is 0.

8. A hydroxy compound selected from the group consisting of:

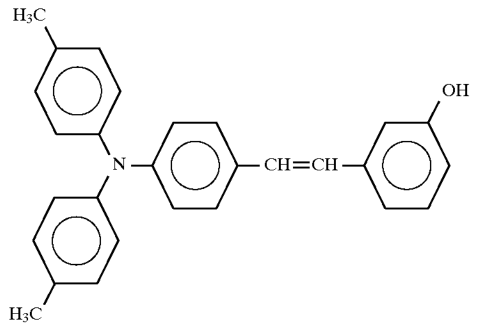

(III)-1

-continued
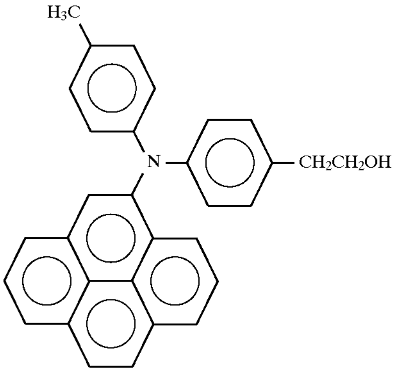
(III)-2
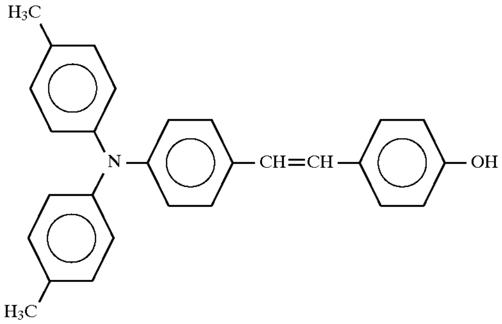
(III)-3
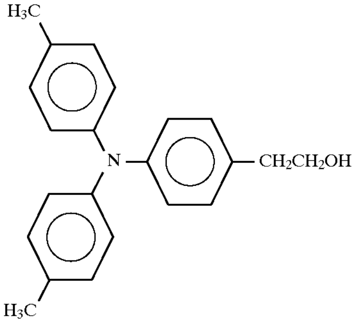
(III)-4
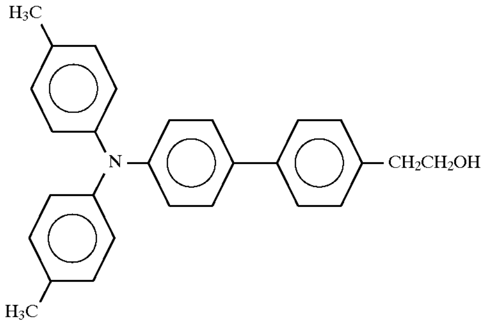
(III)-5
-continued
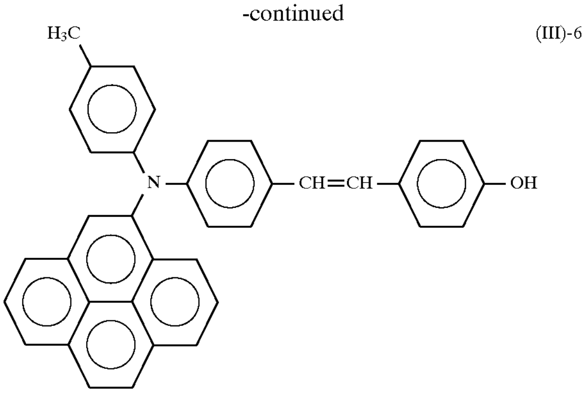
(III)-6
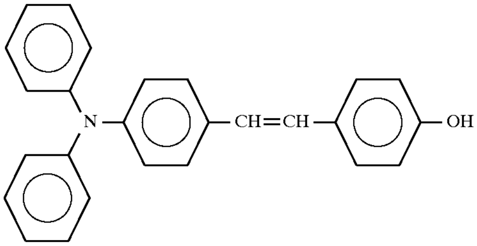
(III)-7
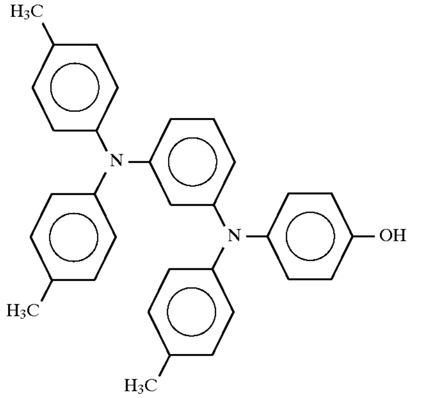
(III)-8
and
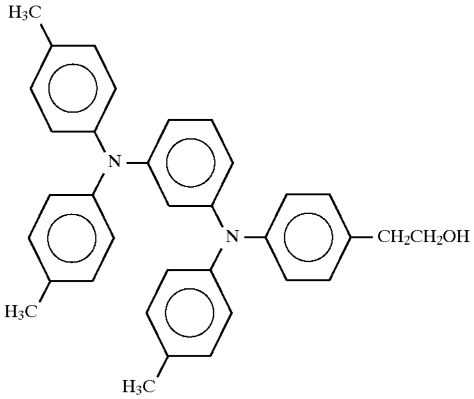
(III)-9
* * * * *

UNITED STATES PATENT AND TRADEMARK OFFICE

CERTIFICATE OF CORRECTION

PATENT NO. : 5,808,155

DATED : September 15, 1998

INVENTOR(S): Tomoyuki SHIMADA ET AL.

It is certified that an error appears in the above-identified patent and that said Letters Patent is hereby corrected as shown below:

Column 33, line 15, "where" should read --there--.

Signed and Sealed this

Nineteenth Day of September, 2000

Attest:

Q. TODD DICKINSON

*Attesting Officer* *Director of Patents and Trademarks*